(12) United States Patent
Huylebroeck et al.

(10) Patent No.: US 7,435,806 B2
(45) Date of Patent: Oct. 14, 2008

(54) NUCLEIC ACID BINDING OF MULTI-ZINC FINGER TRANSCRIPTION FACTORS

(75) Inventors: Danny Huylebroeck, Liedekerke (BE); Kristin Verschueren, Everberg (BE); Jacques Remacle, Hannut (BE)

(73) Assignee: Vlaams Interuniversitair Instituut voor Biotechnologie vzw, Zwijnaarde (BE)

( * ) Notice: Subject to any disclaimer, the term of this patent is extended or adjusted under 35 U.S.C. 154(b) by 172 days.

(21) Appl. No.: 11/196,670

(22) Filed: Aug. 3, 2005

(65) Prior Publication Data

US 2005/0272090 A1   Dec. 8, 2005

Related U.S. Application Data

(63) Continuation of application No. 10/028,396, filed on Dec. 21, 2001, now abandoned, which is a continuation of application No. PCT/EP00/05582, filed on Jun. 9, 2000.

(30) Foreign Application Priority Data

Jun. 25, 1999   (EP)   ................................ 99202068

(51) Int. Cl.
 C07H 21/04   (2006.01)
(52) U.S. Cl. ..................................... 536/23.1; 536/25.6
(58) Field of Classification Search ........................ None
See application file for complete search history.

(56) References Cited

U.S. PATENT DOCUMENTS

| 5,695,936 A * | 12/1997 | Mandrand et al. ............... 435/6 |
| 5,840,489 A * | 11/1998 | Keating et al. .................. 435/6 |
| 6,313,280 B1 | 11/2001 | Verschueren et al. |
| 6,537,751 B1 * | 3/2003 | Cohen et al. .................... 435/6 |

FOREIGN PATENT DOCUMENTS

| EP | 1 192 268 B1 | 11/2005 |
| WO | WO 97/40190 | 10/1997 |
| WO | WO 98/55512 | 12/1998 |
| WO | WO 01/00864 | 1/2001 |

OTHER PUBLICATIONS

Li J J, et al. Science. Dec. 17, 1993; 262 (5141): 1870-4.*
Remacle JE, et al. Nucl Acids Res. Nov. 15, 1998; 26 (22): 5223-4.*
Luo Y, et al. Biotechniques. 1996; 20 (4): 564-8.*
Sekido R, et al. Genes Cells. Dec. 1997; 2 (12): 771-83.*
Genetta T, et al. Mol Cell Biol. Sep. 1994; 14 (9): 6153-63.*
Suzuki T, et al. J Biochem (Tokyo). Aug. 1998; 124 (2): 389-95.*
Houchens CR, et al. Nucleic Acids Res. Jan. 15, 2000; 28 (2): 570-81.*
Blaiseau PL, et al. Mol Cell Biol. Jul. 1997; 17 (7): 3640-8.*
Wadman et al. (EMBO Journal vol. 16, No. 11 pp. 3145-3157, 1997).*
Sekido et al. (Gene vol. 173, pp. 227-232).*

Chien et al., "The two-hybrid system: A method to identify and clone genes for proteins that interact with a protein of interest," Biochemistry, Nov. 1991, pp. 9578-9582, vol. 88, Proc. Natl. Acad. Sci., US.
Choo et al., "Selection of DNA binding sites for zinc fingers using rationally randomized DNA reveals coded interactions," Biochemistry, Nov. 1994, pp. 11168-11172, vol. 91, Proc. Natl. Acad. Sci., US.
Funahashi et al., "Identification of Nuclear Factor δEF1 and its Binding Site Essential for Lens-Specific Activity of the δ1-Crystallin Enhancer," Nucleic Acids Research, 1991, pp. 3543-3547, vol. 19, No. 13.
Ikeda et al., "A fusion protein library: an improved method for rapid screening and characterization of DNA binding or interacting proteins," Gene, 1996, pp. 167-171, vol. 181, Elsevier.
Kamachi et al., "Overlapping Positive and negative Regulatory Elements Determine Lens-Specific Activity of the δ1-Crystallin Enhancer," Molecular and Cellular Biology, Sep. 1993, pp. 5206-5215, vol. 13, No. 9.
Kispert et al., "The Brachyury gene encodes a novel DNA binding protein," The EMBO Journal, 1993, pp. 3211-3220, vol. 12, No. 8.
PCT Communication Relating to the Results of the Partial International Search, PCT/EP00/05582.
PCT International Preliminary Examination Report, PCT/EP00/05582, dated Jun. 25, 1999.
Remacle et al., New mode of DNA binding of multi-zinc finger transcription factors: δEF1 family members bind with two hands to two targets sites, The EMBO Journal, 1999, pp. 5073-5084, vol. 18, No. 18.
Sekido et al., "Organization of the gene encoding transcriptional repressor δEF1 and cross-species conservation of its domains," Gene, 1996, pp. 227-232, vol. 173.
Verschueren et al., "SIPI, a Novel Zinc Finger/Homeodomain Repressor, Interacts with Smad Proteins and Binds to 5'-CACCT Sequences in Candidate Target Genes," The Journal of Biological Chemistry, 1999, pp. 20489-20498, vol. 274, No. 29, The American Society for Biochemistry and Molecular Biology, Inc.

(Continued)

Primary Examiner—Larry R. Helms
Assistant Examiner—Meera Natarajan
(74) Attorney, Agent, or Firm—TraskBritt

(57) ABSTRACT

A method of identifying transcription factors comprising providing cells with a nucleic acid sequence at least comprising a sequence CACCT (SEQ ID NO:1) as bait for the screening of a library encoding potential transcription factors and performing a specificity test to isolate said factors. Preferably, the bait comprises twice the CACCT (SEQ ID NO:1) sequence, more particularly the bait comprises one of the sequences CACCT-N-CACCT (a first SEQ ID NO:1 and a second SEQ ID NO:1 separated by N), CACCT-N-AGGTG (SEQ ID NO:1 and SEQ ID NO:3 separated by N), AGGTG-N-CACCT (SEQ ID NO:3 and SEQ ID NO:1 separated by N), or AGGTG-N-AGGTG (a first SEQ ID NO:3 and a second SEQ ID NO:3 separated by N), wherein N is a spacer sequence. The transcription factors identified using the methods of the invention include separated clusters of zinc fingers, such as, for example, a two-handed zinc finger transcription factor. Also, at least one such zinc finger transcription factor, denominated as SIP1, induces tumor metastasis by down regulation of the expression of E-cadherin. Compounds interfering with SIP1 activity can thus be used to prevent tumor invasion and metastasis.

16 Claims, 2 Drawing Sheets

OTHER PUBLICATIONS

Genetta et al., "Displacement of an E-Box-Binding Repressor by Basic Helix-Loop-Helix Proteins: Implications for B-Cell Specificity of the Immunoglobulin Heavy-Chain Enhancer," Molecular and Cellular Biology, Sep. 1994, pp. 6153-6163, vol. 14, No. 9.

Suzuki et al., "Isolation and Initial Characterization of GBF, a Novel DNA-Binding Zinc Finger Protein That Binds to the GC-Rich Binding Sites of the HIV-1 Promoter," J. Biochem, 1998, pp. 389-395, vol. 124.

Houchens et al., "The dhfr Ori-Beta-Binding Protein RIP60 Contains 15 Zinc Fingers: DNA Binding and Looping by the Central Three Fingers and an Association Proline-Rich Region," Nucleic Acids Research, 2000, pp. 570-581, vol. 28, No. 2.

Blaiseau et al., "Met31p and Met 32p, Two Related Zinc Finger Proteins, Are Involved in Transcriptional Regulation of Yeast Sulfur Amino Acid Metabolism," Molecular and Cellular Biology, Jul. 1997, pp. 3640-3648, vol. 17, No. 7.

Li et al., "Isolation of ORC6, a Component of the Yeast Origin Recognition Complex by a One-Hybrid System," Science, Dec. 17, 1993, pp. 1870-1874, vol. 262, No. 5141.

rRemacle et al., "A Novel Expression Cloning Method to isolate Mammalian Transcription Factors in *Schizosaccharomyces pombe*," Nucleic Acids Research, 1998, pp. 5223-5224, vol. 26, No. 22.

Luo et al., "Cloning and Analysis of DNA-Binding Proteins by Yeast One-Hybrid and One Two-Hybrid Systems," BioTechniques, 1996, pp. 564-568, Vo. 20, No. 4.

Sekido et al., "Two Mechanisms in the Action of Repressor δ-EF1: Binding Site Competition with an Activator and Active Repression," Genes to Cells, 1997, pp. 771-783, vol. 2.

Mak et al., "Examination of mammalian Basic Helix-Loop-Helix Transcription Factors Using a Yeast One-Hybrid System," DNA and Cell Biology, 1996, pp. 1-8, vol. 15. No. 1.

Ruezinsky et al., Modulation of the IgH enhancer's cell type specificity through a genetic switch, Genes & Development, 1991, pp. 29-37, vol. 5, Cold Spring Harbor Laboratory Press.

Kiledjian et al., Identification and Characterization of Two Functional Domains within the Murine Heavy-Chain Enhancer, Molecular and Cellular Biology, Jan. 1988, pp. 145-152, vol. 8, No. 1.

* cited by examiner

NUCLEIC ACID BINDING OF MULTI-ZINC FINGER TRANSCRIPTION FACTORS

CROSS-REFERENCE TO RELATED APPLICATIONS

This application is a continuation of U.S. patent application Ser. No. 10/028,396, filed Dec. 21, 2001, now abandoned, which application is a continuation of International Appln. PCT/EP00/05582 (International Publ. No. WO 01/00864, published Jan. 4, 2001), the contents of the entirety of which is incorporated by this reference, filed on Jun. 9, 2000, designating the United States of America.

TECHNICAL FIELD

The invention relates to biotechnology generally and, more specifically, to a method of identifying transcription factors.

BACKGROUND

Zinc fingers are among the most common DNA binding motifs found in eukaryotes. It is estimated that there are 500 zinc finger proteins encoded by the yeast genome and that perhaps 1% of all mammalian genes encode zinc finger containing proteins. These proteins are classified according to the number and position of the cysteine and histidine residues available for zinc coordination.

The CCHH class, typified by the Xenopus transcription factor IIIA (19), is the largest. These proteins contain two or more fingers in tandem repeats. In contrast, the steroid receptors contain only cysteine residues that form two types of zinc-coordinated structures with four ($C_4$) and five ($C_5$) cysteines (28). Another class of zinc fingers contains the CCHC fingers. The CCHC fingers, which are found in Drosophila, and in mammalian and retroviral proteins, display the consensus sequence $C-N_2-C-N_4-H-N_4-C$ (SEQ ID NO:65) (Refs. 7, 21, 24). Recently, a novel configuration of CCHC finger, of the $C-N_5-C-N_{12}-H-N_4-C$ (SEQ ID NO:66) type, was found in the neural zinc finger factor/myelin transcription factor family (Refs. 11, 12, 36). Finally, several yeast transcription factors such as GAL4 and CHA4 contain an atypical $C_6$ zinc finger structure that coordinates two zinc ions (Refs. 9, 32).

Zinc fingers are usually found in multiple copies (up to 37) per protein. These copies can be organized in a tandem array, forming a single cluster or multiple clusters, or they can be dispersed throughout the protein. Several families of transcription factors share the same overall structure by having two (or three) widely separated clusters of zinc fingers in their protein sequence. The first, the MBPs/PRDII-BF1 transcription factor family, includes Drosophila Schnurri and Spalt genes (1, 3, 6, 14, 33). Both MBP-1 (also known as PRDII-BF1) and MBP-2 contain two widely separated clusters of two CCHH zinc fingers. The overall similarity between MBP-1 and MBP-2 is 51%, but the conservation is much higher (over 90%) for both the N-terminal and the C-terminal zinc finger clusters (33). This indicates an important role of both clusters in the function of these proteins. In addition, the N-terminal and C-terminal zinc finger clusters of MBP-1 are very homologous to each other (3).

The neural specific zinc finger factor 1 and factor 3 (NZF-1 and NZF-3), as well as the myelin transcription factor 1 (MyT1, also known as NZF-2), belong to another family of proteins containing two widely separated clusters of CCHC zinc fingers (11, 12, 36). Like the MBP proteins, different NZF factors exhibit a high degree of sequence identity (over 80%) between the respective zinc finger clusters, whereas the sequences outside of the zinc finger region are largely divergent (36). In addition, each of these clusters can independently bind to DNA, and recognizes similar core consensus sequences (11). NZF-3 binds to a DNA element containing a single copy of this consensus sequence but was shown to exhibit a marked enhancement in relative affinity to a bipartite element containing two copies of this sequence (36). This finding suggests that the NZF factors may also bind to reiterated sequences. However, the mechanism underlying the cooperative binding of NZF-3 to the bipartite element is currently unknown.

The Drosophila Zjh-1 and the vertebrate δEF1 proteins (also known as ZEB or AREB6) belong to a third family of transcription factors. This family is characterized by the presence of two separated clusters of CCHH zinc fingers and a homeodomain-like structure (see, FIG. 1A) (Refs. 4, 5, 35). In δEF1, the N-terminal and C-terminal clusters are also very homologous and were shown to bind independently to very similar core consensus sequences (10). Recently, it was shown that mutant forms of δEF1 lacking either the N-terminal or the C-terminal cluster have lost their DNA binding capacity indicating that both clusters are required for the binding of δEF1 to DNA (31). The Evi-1 transcription factor was shown to contain ten CCHH zinc fingers; seven zinc fingers are present in the N-terminal region, and three zinc fingers are in the C-terminal region (22). With this factor the situation is different from the transcription factors described above, because the two clusters bind to two different target sequences, which are bound simultaneously by full-length Evi-1 (20). Binding of full-length Evi-1 is mainly observed when the two target sequences are positioned in a certain relative orientation, but there was no strict requirement for an optimal spacing between these two targets.

Cell-cell adhesion is predominantly a necessity during cell differentiation, tissue development, and tissue homeostasis. The effect of disrupted cell-cell adhesion is displayed in many cancers, where metastasis and poor prognosis are correlated with loss of cell-cell adhesion. E-cadherin, a homophilic $Ca^{2+}$-dependent transmembrane adhesion molecule, and the associated catenins are among the major constituents of the epithelial cell-junction system. E-cadherin exerts a potent invasion-suppressing role in tumor cell line systems (Refs. 46, 47) and in in vivo tumor model systems (Ref. 48). Loss of E-cadherin expression during tumor progression has been described for more than 15 different carcinoma types (49). Extensive analyses has made clear that aberrant E-cadherin expression as a result of somatic inactivating mutations of both E-cadherin alleles is rare and so far largely confined to diffuse gastric carcinomas and infiltrative lobular breast carcinomas (50, 51). Northern analysis and in situ hybridization studies revealed that reduced E-cadherin immunoreactivity in human carcinomas correlates with decreased mRNA levels (52-54). Analysis of mouse and human E-cadherin promoter sequences revealed a conserved modular structure with positive regulatory elements including a CCAAT-box and a GC-box, as well as two E-boxes (CANNTG) with a potential repressor role (Refs. 55, 56). Mutation analysis of the two E-boxes in the E-cadherin promoter demonstrated a crucial role in the regulation of the epithelial specific expression of E-cadherin. Mutation of these two E-box elements results in the up regulation of the E-cadherin promoter in dedifferentiated cancer cells, where the wild-type promoter shows low activity (55, 56).

SUMMARY OF THE INVENTION

The invention relates to a method of identifying transcription factors involving providing cells with a nucleic acid sequence including a sequence CACCT (SEQ ID NO:1) as bait for the screening of a library encoding potential transcription factors and performing a specificity test to isolate the factors. Transcription factors identified using the method include separated clusters of zinc fingers such as, for example, a two-handed zinc finger transcription factor. At least one such zinc finger transcription factor, denominated "SIP1," induces tumor metastasis by down regulation of the expression of E-cadherin. Compounds interfering with SIP1 activity can thus be used to prevent tumor invasion and metastasis.

The mechanism of DNA binding remains poorly understood for most of the previously identified complex factors. We have characterized the DNA binding properties of vertebrate transcription factors belonging to the emerging family of two-handed zinc finger transcription factors such as δEF1 and SIP1. SIP1 is a member of this transcription factor family, which was recently isolated and characterized as a Smad-interacting protein (Ref. 34). The SIP1 and δEF1, a transcriptional repressor involved in skeletal development and muscle cell differentiation, belong to the same family of transcription factors. They contain two separated clusters of CCHH zinc fingers, which share high sequence identity (>90%). The DNA-binding properties of these transcription factors have been investigated. The N-terminal and C-terminal clusters of SIP1 show high sequence homology as well, and according to the invention each binds to a 5'-CACCT sequence (SEQ ID NO:1). Furthermore, high affinity binding sites for full length SIP1 and δER1 in the promoter regions of candidate target genes like Brachyury, α4-integrin and E-cadherin, are bipartite elements composed of one CACCT sequence (SEQ ID NO:1) and one CACCTG sequence (SEQ ID NO:2). No strict requirement for the relative orientation of both sequences was observed, and the spacing between them (also denominated as N) may vary from 0, 1, 2, 3, 4, 5, 6, 7, 8, 9, 10, ..., to at least 44 bp. For binding to these bipartite elements, the integrity of both SIP1 zinc finger clusters is necessary, indicating that they are both involved in binding to DNA. Furthermore, SIP1 binds as a monomer to a CACCT-$X_N$-CACCTG site (SEQ ID NO:1 and SEQ ID NO:2 separated by $X_N$), by having one zinc finger cluster contacting the CACCT (SEQ ID NO:1), and the other zinc finger cluster binding to the CACCTG sequence (SEQ ID NO:2).

Stable transfection of cells: For stable transfection of the MDCK-Tetoff cell line, the LIPOFECTAMINEPLUS™ (transfection reagent) (Gibco BRL, Rockville, Md.) method was used. 2000 cells were grown on a 75 cm² falcon for 24 hours and then transfected with 30 µg of pUHD10.3-SIP1 plasmid plus 3 µg pPHT plasmid. The latter is a pPNT derivative and confers resistance to hygromycin (80). Stable MDCK-Tetoff transfectants, MDCK-Tetoff-SIP1, were selected by hygromycin-B (150 units/ml) (Duchefa Biochemie, Haarlem, NL) for a period of two weeks, Induction of SIP1 was prevented by adding tetracycline (1 µg/µl) (Sigma Chemicals, US). Expression of SIP1 was done by washing away tetracycline at the time of subcloning. Stable clones with reliable induction properties were identified by immunofluoresence using anti-Myc tag antibodies.

Promoter reporter assays: MCF7/AZ cells were transiently transfected by using FUGENE® (transfection reagent (Roche; Basel, CH). NMe and MDA-MB231 were transfected with the LIPOFECTAMINE™ (transfection reagent) (Gibco BRA; Rockville, Md.) procedure and the parental N4CDK cell line was transiently transfected with LIPOFECTAMINEPLUS™ (transfection reagent) (Gibco BRL; Rockville, Md.). For transient transfection, about 200,000 cells were seeded per 10-cm² well. After incubation for 24 hours 600 ng of each plasmid type DNA was transfected. The medium was refreshed 24 hours after transfection. Cells were lysed after three days in GALACTON-STAR® (chemiluminescence reagent) kit lysis solution (Tropix, Bedford, Mass.). Normalization of transfection was done by measuring β-galactosidase, encoded by the cotransfected pUT651 plasmid (Eurogentec; Seraing, BE). Luciferase substrate is added to each sample. For β-galactosidase detection, a chemiluminescent substrate is supplied (Tropix, Bedford, Mass.). Luciferase and β-galactosidase activity was assayed in a TOPCOUNT® microplate scintillation reader (Packard Instrument Co., Meriden, Conn.).

Northern analysis: Total RNA was isolated with the RNeasy kit (Qiagen; Chatsworth, Calif.) following the manufacturer's protocol. Total RNA (25 µg) was gyoxylated, size-fractionated on a 1% agarose gel and transferred onto a HYBOND™ $-N^+$membrane (Amersham Pharmacia Biotech, Rainhalm, UK). Hybridizations were performed as described before (81). The mouse SIP1 probe (459 bp) was generated by an EcoR-I digest of the mouse SIP1 cDNA. The human SIP1 probe (707 bp) was created by a Bst EII-NotI digest on the Kiaa 0569 clone (Kazusa DNA Research Institute). The mouse E-cadherin probe used was a SacI fragment (500 bp) of the mouse E-cadherin cDNA. Two degenerated primers: 5' CTTCCAGCAGCCCTACGAYCARGCNCA 3' (SEQ ID NO:48) and 5' GGGTGTGGGACCGGATRTG-CATYTTNAT 3' (SEQ ID NO:49) were used to amplify a fragment of the dog Snail cDNA from a total cDNA population of the MDCK cell line. Cloning and sequencing of the amplified band revealed a 432 bp cDNA fragment. To control the amount of loaded RNA, a GAPDH probe was used on the same blot. We performed the quantification of the radioactive bands on a PHOSPHORIMAGER® (image reader) 425 (Bio-Rad, Richmond, Calif.).

The transcription factor(s) identified using a method according to the invention comprises separated clusters of zinc fingers such as, for example, two-handed zinc finger transcription factors.

These sequences may originate from any promoter region, but preferably from the group (also referred to as "target genes") selected from Brachyury, α4-integrin, follistatin or E-cadherin.

The invention includes the transcription factors obtainable by and produced by a method according to the invention.

In another embodiment, the invention relates to a method of identifying, isolating, and/or producing compounds with an interference capability towards transcription factors, obtained as described herein. For example, the invention includes a method involving adding a sample comprising a potential compound to be identified to a test system comprising (i) a nucleotide sequence comprising one of a first SEQ ID NO:1 and a second SEQ ID NO:1 separated by N, SEQ ID NO:1 and SEQ ID NO:3 separated by N, SEQ ID NO:3 and SEQ ID NO:1 separated by N, or a first SEQ ID NO:3 and a second SEQ ID NO:3 separated by N, wherein N, in these sequences, is a spacer sequence as previously described, (ii) a protein capable to bind the nucleotide sequence, incubating the sample in the system for a period sufficient to permit interaction of the compound or its derivative or counterpart thereof with the protein and comparing the amount and/or activity of the protein bound to the nucleotide sequence before and after the addition.

Comparison of the amount of protein bound to the nucleotide sequence before and after adding the test sample can be accomplished, for example, by using a gel band-shift assay or a filter-binding assay. As a next step the compound thus identified can be isolated and optionally purified and further analyzed according to methods known to persons skilled in the art. The protein in step a) (ii) can be any protein capable to bind the nucleotide sequence, but is preferably a Smad-interacting protein such as SIP1.

Compounds identified by the latter method are also part of the present invention. With the term "compounds with an interference capability towards transcription factors" is meant compounds, which are able to modulate (e.g., to inhibit, to weaken, and/or to strengthen) the bioactivity of transcription factors. More specifically, the latter compounds are able to completely or partially inhibit the production and/or bioactivity of SIP1. Examples of such compounds are small molecules or anti-SIP1 antibodies or functional fragments derived thereof specifically binding to SIP1 protein or anti-sense nucleic acids or ribozymes binding to mRNA encoding SIP1 or small molecules binding the promoter region bound by SIP1. In this regard, the present invention relates to compounds that modulate regulation of E-cadherin expression by SIP1. More specifically, the present invention relates to compounds that, via inhibiting SIP1 production and/or activity prevent the down-regulation of the expression of the target gene E-cadherin. In other words, the present invention relates to compounds that can be used as a medicament to prevent or treat tumor invasion and/or metastasis, which is due to the down-regulation of E-cadherin expression by SIP-1. Methods to produce and use the latter compounds are exemplified further.

The invention also includes a test kit to perform the method comprising at least (i) an nucleotide sequence comprising one of a first SEQ ID NO:1 and a second SEQ ID NO:1 separated by N, SEQ ID NO:1 and SEQ ID NO:3 separated by N, SEQ ID NO:3 and SEQ ID NO:1 separated by N, or a first SEQ ID NO:3 and a second SEQ ID NO:3 separated by N, wherein N, in these sequences, is a spacer sequence as previously described, and (ii) a protein capable of binding the nucleotide sequence.

In another embodiment, the invention concerns an alternative to the so-called "two hybrid" screening assay as disclosed in the prior art. Several means and methods have been developed to identify binding partners of proteins. This has resulted in the identification of a number of respective binding proteins. Many of these proteins have been found using so-called "two hybrid" systems. Two-hybrid cloning systems have been developed in several labs (Chien et al., 1991; Durfee et al., 1993; Gyuris et al., 1993). All have three basic components: Yeast vectors for expression of a known protein fused to a DNA-binding domain, yeast vectors that direct expression of cDNA-encoded proteins fused to a transcription activation domain, and yeast reporter genes that contain binding sites for the DNA-binding domain. These components differ in detail from one system to the other. All systems utilize the DNA binding domain from either Gal4 or LexA. The Gal4 domain is efficiently localized to the yeast nucleus where it binds with high affinity to well-defined binding sites that can be placed upstream of reporter genes (Silver et al., 1986). LexA does not have a nuclear localization signal, but enters the yeast nucleus and, when expressed at a sufficient level, efficiently occupies LexA binding sites (operators) placed upstream of a reporter gene (Brent et al., 1985). No endogenous yeast proteins bind to the LexA operators. Different systems also utilize different reporters. Most systems use a reporter that has a yeast promoter, either from the GAL1 gene or the CYC1 gene, fused to lacZ (Yocum et al., 1984). These lacZ fusions either reside on multicopy yeast plasmids or are integrated into a yeast chromosome. To make the lacZ fusions into appropriate reporters, the GAL1 or CYC1 transcription regulatory regions have been removed and replaced with binding sites that are recognized by the DNA-binding domain being used. A screen for activation of the lacZ reporters is performed by plating yeast on indicator plates that contain X-Gal (5-bromo-4-chloro-3-indolyl-p-D-galactoside); on this medium, yeast (in which the reporters are transcribed) produces beta-galactosidase and turns blue. Some systems use a second reporter gene and a yeast strain that requires expression of this reporter to grow on a particular medium. These "selectable marker" genes usually encode enzymes required for the biosynthesis of an amino acid. Such reporters have the marked advantage of providing an election for cDNAs that encode interacting proteins, rather than a visual screen for blue yeast. To make appropriate reporters from the marker genes, their upstream transcription regulatory elements were replaced by binding sites for a DNA-binding domain. The HIS3 and LEU2 genes have both been used as reporters in conjunction with appropriate yeast strains that require their expression to grow on media lacking either histidine or leucine, respectively. Finally, different systems use different means to express activation-tagged cDNA proteins.

In all current schemes, the cDNA-encoded proteins are expressed with an activation domain at the amino terminus. The activation domains used include the strong activation domain from Gal4, the very strong activation domain from the Herpes simplex virus protein VP16, or a weaker activation domain derived from bacteria, called B42. The activation-tagged cDNA-encoded proteins are expressed either from a constitutive promoter, or from a conditional promoter such as that of the GAL1 gene. Use of a conditional promoter makes it possible to quickly demonstrate that activation of the reporter gene is dependent on expression of the activation-tagged cDNA proteins.

It is clear from the foregoing that two-hybrid systems for finding binding proteins have been used in the past. However, although the conventional two hybrid system has proven to be a valuable tool in finding proteinaceous molecules that can bind to other proteins it is an artificial system. A characteristic of a two hybrid system is that a fusion protein is made consisting of a part of which binding partners are sought and a reporter part that enables detection of binding. For finding relevant binding partners, several criteria must be met of which one is of course the correct choice of the region in the protein where binding to other proteins occurs. Another criterion which is much more difficult if not impossible to predict accurately on forehand is obtaining correct folding of the region (i.e., a folding of the region sufficiently similar to the folding of the region in the natural protein). Correct folding depends on among other things, the actual amino acid sequence chosen for generating the fusion protein. Another factor determining the identification of relevant binding partners is the sensitivity with which binding can be detected.

An alternative to the conventional two-hybrid system is also provided herein. Thus, the invention provides an in vivo method and kit for detecting interactions between proteins and the influence of other compounds on the interaction as such, using reconstitution of the activity of a transcriptional activator. This reconstitution makes use of two, so-called hybrid, chimeric, or fused proteins. These two fused proteins each show, independent from one another, a weak affinity towards a nucleic acid sequence comprising one of a first SEQ ID NO:1 and a second SEQ ID NO:1 separated by N, SEQ ID NO:1 and SEQ ID NO:3 separated by N, SEQ ID NO:3 and SEQ ID NO:1 separated by N, or a first SEQ ID NO:3 and a second SEQ ID NO:3 separated by N, wherein N, in these sequences, is a spacer sequence as previously described. However, when both fused proteins are independently bound to the sequence, and the test proteins each available in each of two fused proteins are as a result thereof brought into close proximity, the binding affinity towards the nucleic acid sequence comprising one of a first SEQ ID NO:1 and a second SEQ ID NO:1 separated by N, SEQ ID NO:1 and SEQ ID NO:3 separated by N, SEQ ID NO:3 and SEQ ID NO:1 separated by N, or a first SEQ ID NO:3 and a second SEQ ID NO:3 separated by N, wherein N, in these sequences, is a spacer sequence as previously described, becomes much stronger. If the two test proteins indeed are able to interact, they bring, as a consequence thereof, into close proximity the transcriptional activator's two domains. This proximity is sufficient to cause transcription, which can be detected by the activity of a marker gene located adjacent to the nucleic acid sequence comprising one of a first SEQ ID NO:1 and a second SEQ ID NO:1 separated by N, SEQ ID NO:1 and SEQ ID NO:3 separated by N, SEQ ID NO:3 and SEQ ID NO:1 separated by N, or a first SEQ ID NO:3 and a second SEQ ID NO:3 separated by N, wherein N, in these sequences, is a spacer sequence as previously described.

In accordance herewith a method is provided for detecting an interaction between a first interacting protein and a second interacting protein comprising providing a suitable host cell with a first fusion protein comprising a first interacting protein fused to a DNA binding domain capable to bind a nucleic acid sequence comprising one of a first SEQ ID NO:1 and a second SEQ ID NO:1 separated by N, SEQ ID NO:1 and SEQ ID NO:3 separated by N, SEQ ID NO:3 and SEQ ID NO:1 separated by N, or a first SEQ ID NO:3 and a second SEQ ID NO:3 separated by N, wherein N, in these sequences, is a spacer sequence as previously described, providing the suitable host cell with a second fusion protein comprising a second interacting protein fused to a DNA binding domain capable to bind a nucleic acid sequence comprising one of a first SEQ ID NO:1 and a second SEQ ID NO:1 separated by N, SEQ ID NO:1 and SEQ ID NO:3 separated by N, SEQ ID NO:3 and SEQ ID NO:1 separated by N, or a first SEQ ID NO:3 and a second SEQ ID NO:3 separated by N, wherein N, in these sequences, is a spacer sequence as previously described, subjecting the host cell to conditions under which the first interacting protein and the second interacting protein are brought into close proximity and determining whether a detectable gene present in the host cell and located adjacent to the nucleic acid sequence has been expressed to a degree greater than expressed in the absence of the interaction between the first and the second interacting protein.

As an example, it should be clear that, in case a binding partner (prey) for a specific protein (bait) has been identified, the first fusion protein containing the bait will for example bind to the sequence CACCT (SEQ ID NO:1) (or AGGTG (SEQ ID NO:3)) of the sequence CACCT-N-AGGTG and that the second fusion protein containing the prey will bind to the sequence AGGTG, (SEQ ID NO:3) (or CACCT (SEQ ID NO:1)) of the sequence CACCT-N-AGGTG so that transcription of a marker gene will occur.

The present invention finally relates to the new sequences a first SEQ ID NO:1 and a second SEQ ID NO:1 separated by N, SEQ ID NO:1 and SEQ ID NO:3 separated by N, SEQ ID NO:3 and SEQ ID NO:1 separated by N, and a first SEQ ID NO:3 and a second SEQ ID NO:3 separated by N, wherein N, in these sequences, is a spacer sequence as previously described, and to the use of the sequences, in addition to any other sequence at least comprising a sequence CACCT (SEQ ID NO:1), for the identification, via any method known by a person skilled in the art, of new target genes different from the already described target genes Brachyury, α4-integrin, follistatin or E-cadherin.

DETAILED DESCRIPTION OF THE INVENTION

Figure 1:
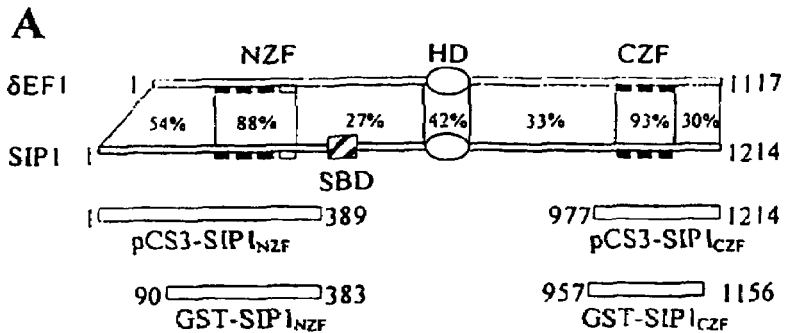
FIG. 1 is a schematic representation of Zfh-1, SIP1 and δEF1, and alignment of the SIP1 and δEF1 zinc fingers. (A) Schematic representation of mouse δEF1 (1117 amino acids) and SIP1 (1214 amino acids). The filled boxes represent CCHH zinc fingers, the open boxes are CCHC zinc fingers. The homeodomain-like domain (HD) is depicted as an oval. The percentage represents the homology between different domains. SIP1 polypeptides used in this study are depicted with their coordinates. SBD: Smad-binding domain (Verschueren et al., 1999). (B) Alignments of the amino acid sequences from zinc fingers of SIP1 and δEF1. Vertical bars indicate sequence identity. The conserved cysteine and histidine residues forming the zinc fingers are printed in bold, and indicated by an asterisk. The residues in zinc fingers that can contact DNA are indicated with an arrow. (C) Alignment of the protein sequence of $SIP1_{NZF3+NZF4}$ and $SIP1_{CZF2+CZF3}$, and of $δEF1_{NZF3+NZF4}$ and $δEF1_{CZF2+CZF3}$, respectively, demonstrating intramolecular conservation of zinc fingers.

The following definitions are set forth to assist in the understanding of various terms used herein.

"Nucleic acid" or "nucleic acid sequence" or "nucleotide sequence" means genomic DNA, cDNA, double stranded or single stranded DNA, messenger RNA or any form of nucleic acid sequence known to one of skill in the art.

The terms "protein" and "polypeptide" used in this application are interchangeable. "Polypeptide" refers to a polymer of amino acids (amino acid sequence) and does not refer to a specific length of the molecule. Thus, peptides and oligopeptides are included within the definition of polypeptide. Included within the definition are, for example, polypeptides containing one or more analogs of an amino acid (e.g., unnatural amino acids, etc.), polypeptides with substituted linkages, as well as other modifications known in the art, both naturally occurring and non-naturally occurring. The proteins and polypeptides described above are not necessarily translated from a designated nucleic acid sequence; the polypeptides may be generated in any manner, including for example, chemical synthesis, or expression of a recombinant expression system, or isolation from a suitable viral system.

The polypeptides may include one or more analogs of amino acids, phosphorylated amino acids, or unnatural amino acids. Methods of inserting analogs of amino acids into a sequence are known in the art. The polypeptides may also include one or more labels, which are known to those skilled in the art. In this context, it is also understood that the proteins may be further modified. By providing the proteins it is also possible to determine fragments, which retain biological activity, namely, the mature, processed form. This allows the construction of chimeric proteins and peptides comprising an amino sequence derived from the mature protein, which is crucial for its binding activity. The other functional amino acid sequences may be either physically linked by, for example, chemical means to the proteins or may be fused by recombinant DNA techniques well known in the art.

The term "derivative," "functional fragment of a sequence" or "functional part of a sequence" means a truncated sequence of the original reference sequence. The truncated sequence (nucleic acid or protein) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids.

The terms "gene(s)," "polynucleotide," "nucleic acid sequence," "nucleotide sequence," "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog.

A "coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

With "transcription factor" is meant a class of proteins that bind to a promoter or to a nearby sequence of DNA to facilitate or prevent transcription initiation.

With "promoter" is meant an oriented DNA sequence recognized by the RNA polymerase holoenzyme to initiate transcription.

With "RNA polymerase" is meant a multi-subunit enzyme that synthesizes RNA complementary to the DNA template.

With "holoenzyme" is meant an active form of enzyme that consists of multiple subunits.

The term "antibody" or "antibodies" refers to an antibody characterized as being specifically directed against a transcription factor such as SIP-1or any functional derivative thereof, with the antibodies being preferably monoclonal antibodies; or an antigen-binding fragment thereof, of the F(ab')$_2$, F(ab) or single chain Fv type, or any type of recombinant antibody derived thereof. Monoclonal antibodies can for instance be produced by a hybridoma liable to be formed according to classical methods from an animal's splenic cells, particularly of a mouse or rat immunized against SIP1 or any functional derivative thereof, and of cells of a myeloma cell line, and to be selected by the ability of the hybridoma to produce the monoclonal antibodies recognizing SIP1 or any functional derivative thereof which have been initially used for the immunization of the animals. Monoclonal antibodies may be humanized versions of mouse monoclonal antibodies made by means of recombinant DNA technology, departing from the mouse and/or human genomic DNA sequences coding for H and L chains or from cDNA clones coding for H and L chains. Alternatively, the monoclonal antibodies may be human monoclonal antibodies. Such human monoclonal antibodies are prepared, for instance, by means of human peripheral blood lymphocytes (PBL) repopulation of severe combined immune deficiency (SCID) mice as described in International Patent Application PCT/EP 99/03605 or by using transgenic non-human animals capable of producing human antibodies as described in U.S. Pat. No. 5,545,806, the contents of both of which are incorporated by this reference. Also, fragments derived from these monoclonal antibodies such as Fab, F(ab)'$_2$ and ssFv ("single chain variable fragment"), form part of the present invention provided that they have retained the original binding properties. Such fragments are commonly generated by, for instance, enzymatic digestion of the antibodies with papain, pepsin, or other proteases. It is well known to the person skilled in the art that monoclonal antibodies, or fragments thereof, can be modified for various uses. The antibodies can also be labeled with an appropriate label of the enzymatic, fluorescent, or radioactive type.

The terms "small molecules" refer to, for example, small organic molecules, and other drug candidates, which can be obtained, for example, from combinatorial and natural product libraries via methods well known in the art. Random peptide libraries consisting of all possible combinations of amino acids attached to a solid phase support may be used to identify peptides that are able to bind to SIP1 or to the promoter region bound by SIP1. The screening of peptide libraries may have therapeutic value in the discovery of pharmaceutical agents that act to inhibit the biological activity of SIP1.

The terms "anti-sense nucleic acids" and "ribozymes" refer to molecules that function to inhibit the translation of SIP1 mRNA. Anti-sense nucleic acids or anti-sense RNA and DNA molecules act to directly block the translation of mRNA by binding to targeted mRNA and preventing protein translation. Ribozymes are enzymatic RNA molecules capable of catalyzing the specific cleavage of RNA. Ribozymes' mechanism of action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of SIP1 RNA sequences. Specific ribozyme cleavage sites within any potential RNA target are initially identified by scanning the target molecule for ribozyme cleavage sites (e.g., GUA, GUU and GUC). Once identified, short RNA sequences of between 15 and 20 ribonucleotides corresponding to the region of the target gene containing the cleavage site may be evaluated for predicted structural features such as secondary structure that may render the oligonucleotide sequence unsuitable. A candidate target's suitability may also be evaluated by testing its accessibility to hybridization with complementary oligonucleotides, using ribonuclease protection assays. Both anti-sense RNA and DNA molecules and ribozymes of the invention may be prepared, for example, by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize anti-sense RNA constitutively or inducibly, depending on the promoter used, can be introduced stably into cell lines.

The mentioned antibodies, small molecules, anti-sense nucleic acids, and ribozymes can be used as "a medicament" to prevent and/or treat tumor invasion and/or metastasis via inhibiting the down-regulation of E-cadherin expression by SIP-1. Malignancy of tumors implies an inherent tendency of the tumor's cells to metastasize (invade the body widely and become disseminated by subtle means) and eventually to kill the patient unless all the malignant cells can be eradicated. Metastasis is thus the outstanding characteristic of malignancy. Metastasis is the tendency of tumor cells to be carried from their site of origin by way of the circulatory system and other channels, which may eventually establish these cells in almost every tissue and organ of the body. In contrast, the cells of a benign tumor invariably remain in contact with each other in one solid mass centered on the site of origin. Because of the physical continuity of benign tumor cells, they may be removed completely by surgery if the location is suitable. But the dissemination of malignant cells, each one individually possessing (through cell division) the ability to give rise to new masses of cells (new tumors) in new and distant sites, precludes complete eradication by a single surgical procedure in all but the earliest period of growth. It should be clear that the "medicament" of the present invention could be used in combination with any other tumor therapy known in the art such as irradiation, chemotherapy or surgery.

With regard to the above-mentioned small molecules, the term "medicament" relates to a composition comprising small molecules as described above and a pharmaceutically acceptable carrier or excipient (both terms can be used interchangeably) to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers.

The "medicament" may be administered by any suitable method within the knowledge of the skilled man. The preferred route of administration is parenterally. In parental administration, the medicament of this invention will be formulated in a unit dosage injectable form such as a solution, suspension or emulsion, in association with the pharmaceutically acceptable excipients as defined above.

However, the dosage and mode of administration will depend on the individual. Generally, the medicament is administered so that molecule of the present invention is given at a dose between 1 μg/kg and 10 mg/kg, more preferably between 10 μg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 μg/kg/minute, more preferably between 7 and 15 μg/kg/minute.

With regard to antibodies, anti-sense nucleic acids, and ribozymes, a preferred mode of administration of the "medicament" for treatment is the use of gene therapy to deliver the above-mentioned molecules. Gene therapy means the treatment by the delivery of therapeutic nucleic acids to patient's cells. This is extensively reviewed in Lever and Goodfellow 1995, *Br. Med Bull.*, 51, 1-242 (Culver 1995); Ledley, F. D., *Hum. Gene Ther.* 6, 1129 (1995). To achieve gene therapy there must be a method of delivering genes to the patient's cells and additional methods to ensure the effective production of any therapeutic genes. Two general approaches exist to achieve gene delivery; these are non-viral delivery and virus-mediated gene delivery.

The following examples more fully illustrate preferred features of the invention, but should not be construed to limit the invention in any way.

EXAMPLES

Characterization of nucleic acid sequences at least comprising a CACCT (SEQ ID NO:1) sequence.

SIP1 and δEF1 Bind to Target Sites Containing One CACCT (SEQ ID NO:1) Sequence and One CACCTG (SEQ ID NO:2) Sequence The DNA binding properties of SIP1 were studied. SIP1, a recently isolated Smad-interacting protein, belongs to the emerging family of two-handed zinc finger transcription factors (34). The organization of SIP1 is very similar to that of δEF1, the prototype member of this family. Both proteins contain two widely separated clusters of zinc fingers, which are involved in binding to DNA. The amino acid sequence homology is very high (more than 90%) within these two zinc finger clusters, whereas it is less evident in the other regions. This finding suggests that both proteins would bind in an analogous fashion to similar DNA targets. Indeed, SIP1 as well as δEF1 bind with comparable affinities to many different target sites, which always contain two CACCT (SEQ ID NO:1) sequences.

$SIP1_{FS}$ inhibits Xbra2 expression when over-expressed in the *Xenopus* embryo (34), and $SIP1_{FS}$ binds to the Xbra2 promoter by contacting two CACCT (SEQ ID NO:1) sequences. Recent studies using *Xenopus* transgenic embryos have shown that 2.1 kb of Xbra2 promoter sequences suffice to express a reporter protein in the same domain as Xbra itself (17). However, a single point mutation within the downstream CACCT (SEQ ID NO:1) site (Xbra-D) in the promoter that disrupts SIP1 binding (as seen in gel retardation assays) has a severe effect. Expression of the marker protein initiates earlier (i.e., at stage 9), and is now found at ectopic sites, for example, in the majority of ectodermal, mesodermal, and endodermal cells (17). This finding indicates that this nucleotide, which is located within the downstream CACCT (SEQ ID NO:1) site, is required for correct spatial and temporal expression of the Xbra2 gene. In addition, when a mutation is introduced in the upstream CACCT (SEQ ID NO:1) sequence, we observed the same premature and ectopic expression of Xbra2 as for the mutation within the downstream CACCT (SEQ ID NO:1) site. Therefore, mutations in either the downstream or upstream CACCT (SEQ ID NO:1) that are known to affect SIP1 or δEF1 binding in EMSA, give the same phenotype in vivo, indicating that a *Xenopus* δEF1-like protein participates in the regulation of the Xbra2 gene. In addition, these in vivo data support the conclusions from the in vitro binding experiments presented here: SIP1/δEF1-like transcription factors require two CACCT (SEQ ID NO:1) sites for regulating the expression of the Xbra2 promoter.

Not all promoter regions containing two CACCT (SEQ ID NO:1) sequences represent SIP1 or δEF1 binding sites. Notably, duplication of the Xbra-F probe, which contains the upstream CACCT (SEQ ID NO:1) sequence present in the Xbra-WT element, is refractory to binding of either SIP1 or δEF1. Moreover, neither $SIP1_{NZF}$ nor $SIP1_{CZF}$ can bind efficiently to this site (Xbra-F) as monomer or as dimer. Thus other sequences in addition to CACCT (SEQ ID NO:1) may be required for generating a high-affinity binding site. It appears that CACCTG (SEQ ID NO:2) is always a better target site for binding of these zinc finger clusters. Indeed, the high-affinity CACCTG (SEQ ID NO:2) site (Xbra-E) was shown to bind either the SIP1$_{NZF}$ or the SIP1$_{CZF}$ cluster. In addition, modification of the CACCTG (SEQ ID NO:2) site into CACCT<u>A</u> strongly affects the binding of SIP1$_{FS}$ and δEF1 to the Xbra promoter, confirming the importance of this 3'-guanine residue. By comparing the sequence of all the SIP1 and δEF1 target sites, a minimal consensus sequence was found composed of one CACCT (SEQ ID NO:1) sequence and one CACCTG (SEQ ID NO:2) sequence, demonstrating that these two sequences are sufficient to form a high-affinity binding site for SIP1 or δEF1.

Although the upstream CACCT (SEQ ID NO:1) sequence is unable to bind SIP1$_{CZF}$ or SIP1$_{NZF}$, this sequence is contacted by full size SIP1 in the context of the Xbra-WT probe. The upstream CACCT (SEQ ID NO:1) sequence is a prerequisite for the binding of SIP1$_{FS}$ to the Xbra-WT probe. Thus, when the upstream CACCT (SEQ ID NO:1) sequence is combined with another, high-affinity CACCTG (SEQ ID NO:2) site (Xbra-E), this low affinity site (Xbra-F) becomes committed to the binding of SIP1$_{FS}$. A model in which SIP1$_{FS}$ contacts its target promoter via the binding of one of its zinc fingers clusters to a high affinity CACCTG (SEQ ID NO:2) sequence (e.g., Xbra-E) is favored, which is followed by the contact of the low affinity CACCT (SEQ ID NO:1) site (Xbra-F) by the second cluster, and this additional interaction strongly stabilizes SIP1 binding. Therefore, a CACCT (SEQ ID NO:1) site may still have an important function in the regulation of gene expression; while even on its own it neither binds SIP1$_{NZF}$, SIP1$_{CZF}$ nor SIP1$_{FS}$.

The DC5 probe from the δ1-crystallin enhancer binds δEF1 specifically (31). However, this probe contains only one CACCT (SEQ ID NO:1) sequence. Therefore, despite having demonstrated here that high affinity binding sites for δEF1 should contain one CACCT (SEQ ID NO:1) sequence and one CACCTG (SEQ ID NO:2) sequence, it cannot be excluded that in particular cases, such as the DC5 probe, one CACCT (SEQ ID NO:1) site would be sufficient for the binding of this type of transcription factor.

Mode of SIP1 DNA Binding

Figure 2:
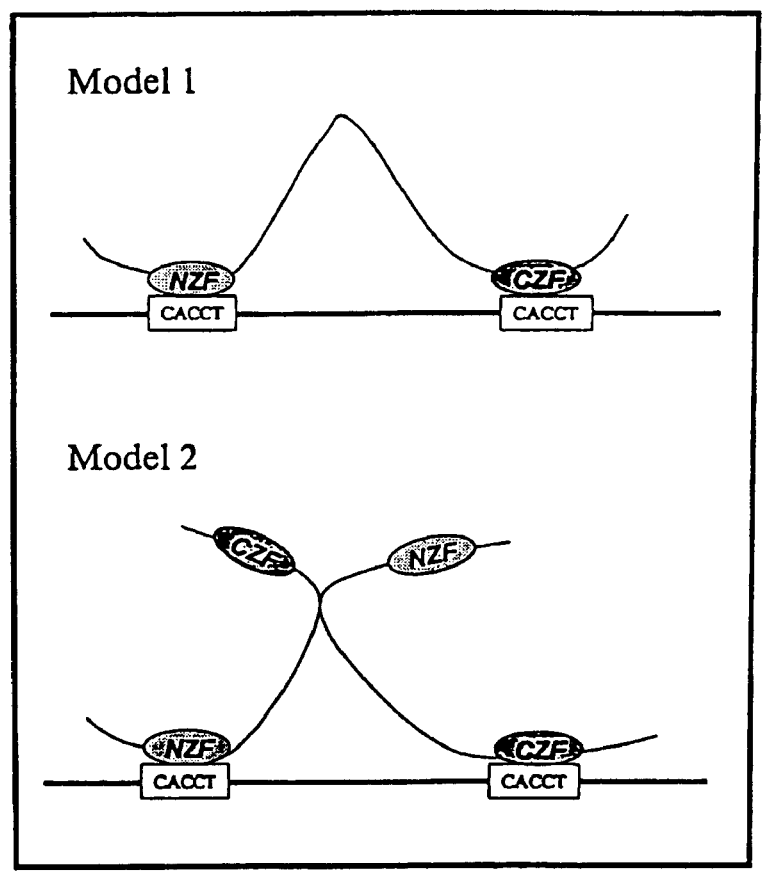
FIG. 2 depicts possible DNA-binding mechanisms for SIP1. Model 1: SIP1 binds DNA as a monomer. Model 2: SIP1 binds DNA as a dimer.

When tested independently in EMSA, both the C-terminal as well as the N-terminal zinc finger clusters of SIP1 or δEF1 bind to very similar CACCT (SEQ ID NO:1) containing consensus sequences. Both for SIP1 and δEF1, δZF3 and NZF4 share an extensive amino acid sequence homology with CZF2 and CZF3, respectively. This homology may explain why these two clusters can bind to similar consensus sequences. In addition, it has been shown that SIP1 or δEF1 require two CACCT (SEQ ID NO:1) sequences for binding to several potential target sites. Based on these results, it is surmised that SIP1 and δEF1 would bind to their target elements in such a way that one zinc finger cluster contacts one of the CACCT (SEQ ID NO:1) sites, while the other cluster contacts the second CACCT (SEQ ID NO:1) site (see, FIG. 2, "Model 1"). An alternative model could be that SIP1 or δEF1 homodimerizes before being able to bind to these target sites with high affinity ("Model 2"). The DNA binding capacity of SIP1$_{NZF}$ is abolished by mutations in either NZF3 or NZF4. Similarly, mutations within CZF2 or CZF3 also affect the binding capacity of SIP$_{1CZF}$. When these mutations are introduced in the context of the full size SIP1, binding of SIP1$_{FS}$ is no longer observed. This observation indicates that the binding activity of both zinc finger clusters is required for the binding of SIP1$_{FS}$ to its target element, containing a doublet of CACCT (SEQ ID NO:1) sites. Similarly, it was previously shown that the integrity of both zinc finger clusters of δEF1 is needed for binding DNA (31). These observations indicate that both zinc fingers clusters are directly contacting the DNA. Therefore, in the dimer model (FIG. 2, Model 2), the SIP1$_{NZF}$ of one SIP1 molecule should bind to one CACCT (SEQ ID NO:1) sequence and the SIP1$_{CZF}$ of the second SIP1 molecule should contact the other CACCT (SEQ ID NO:1) sequence. If such a dimer configuration exists, then it can be assumed that certain combinations of full size SIP1 molecules having different mutations within CZF or NZF, respectively, should allow for the formation of a functional dimer able to bind to its target DNA. None of the possible combinations of the four SIP1$_{FS}$ mutants tested (NZF3mut, NZF4mut, CZF2mut and CZF3mut) gave rise to a DNA/SIP1 complex in EMSAs. This finding argues against the existence of SIP1 dimers. In addition, using differently tagged SIP1$_{FS}$ molecules, detection of SIP1 dimers in EMSAs was not possible, nor to supershift such dimeric complexes with different antibodies. Therefore, support is provided for "Model 1" in which SIP1 binds as a monomer to a target site, which contains one CACCT (SEQ ID NO:1) sequence and one CACCTG (SEQ ID NO:2) sequence.

It has been shown herein that neither the relative orientation of the two CACCT (SEQ ID NO:1) sequences nor the spacing between these sequences is critical for the binding of SIP1$_{FS}$ or δEF1. This showing demonstrates that these transcription factors should display a highly flexible secondary structure to accommodate the binding to these different target sites. The long linker region between the two zinc finger clusters within SIP1 and δEF1 may permit this flexibility in the secondary structure of these proteins. These transcription factors can bind to sites containing CACCT (SEQ ID NO:1) sequences separated by at least 44 bp (Ecad-WT), suggesting that a region of about 50 bp of promoter sequences might be covered and therefore less accessible to transcriptional activators once SIP1$_{FS}$ or δEF1 is bound to this promoter. This indicates that SIP1 or δEF1 could function as transcriptional repressor by competing with transcriptional activators that bind in this region covered by SIP1 or δEF 1.

Other Families of Transcription Factors may Bind DNA with a Similar Mechanism as SIP1

This new mode of DNA binding may also be generalized to other transcription factor families, which, like SIP1 and δEF1, contain separated clusters of zinc fingers like those of the MBP/PRDII-BF1 family (Refs. 1, 3, 6, 29, 33). As with SIP1 and δEF1, the conservation of these zinc finger clusters is very strong between the different members of this family (1). In addition, the C-terminal cluster is very homologous to the N-terminal cluster and, in the case of PRDII-BF1, these clusters bind to the same sequences when tested independently (3). Therefore, this type of transcription factor may bind to two reiterated sequences through the contact of one zinc finger cluster with one sequence and the other cluster with the second sequence. Similarly, the different members of the NZF family of transcription factors also have two widely separated clusters of zinc fingers (Refs. 11, 12, 36). MyT1, NZF-1 and NZF-3 all bind to the same consensus element AAAGTTT (SEQ ID NO:4). Like for SIP1 and δEF1, showing a significantly higher affinity to elements containing two CACCT (SEQ ID NO:1) sequences, an element containing two AAAGTTT (SEQ ID NO:4) sequences demonstrated a markedly higher affinity to NZF-3 (36). This suggests that two AAAGTTT (SEQ ID NO:4) sequences are needed to create a high-affinity binding site for these transcription factors, and that they may bind DNA with a similar mechanism as SIP1 and δEF1. Finally, the Evi-1 protein, which contains seven zinc fingers at the N-terminus and three zinc fingers at the C-terminus, binds to two consensus sequences. It binds to a complex consensus sequence (GACAAGATAAGATAA-N$_{1-28}$-CTCATCTTC (SEQ ID NO:5)) via a mechanism that may involve the binding of the N-terminal zinc finger cluster to the first part and the binding of the C-terminal cluster to the second part (20). In conclusion, the mode of DNA-binding that is described here may not only be applicable to the SIP1/δEF1 family of transcription factors, but appears to be more universal.

SIP1 was cloned as a Smad1-interacting protein but was also shown to interact with Smad2, 3 and 5 (34). Smad proteins are signal transducers involved in the BMP/TGF-β signaling cascade (13). Upon binding of TGF-β ligands to the serine/threonine kinase receptor complex, the receptor-regulated Smad proteins are phosphorylated by type I receptors, and migrate to the cell nucleus where they modulate transcription of target genes. The interaction between SIP1 and Smads has only been observed upon ligand stimulation, indicating that Smads need to be activated before they are capable of interacting with SIP1 (34). Surprisingly, Evi-1, a transcription factor that may bind DNA with a similar mechanism as SIP1, is a Smad3-interacting protein (15). So far, it was shown that Evi-1 inhibited the binding of Smad3 to DNA, but certainly has an effect on target promoters of Evi-1. Schnurri, which is the *Drosophila* homologue of the human PRDII-BF1 transcription factor, is a protein that may also bind DNA with a similar mechanism as SIP1 protein. Interestingly, Schnurri was proposed to be a nuclear protein target in the dpp-signaling pathway (1, 6). Dpp is a member of the TGF-β family. This makes Schnurri a candidate nuclear target for *Drosophila* Mad protein, the *Drosophila* homologue of vertebrate Smads. Therefore, the mode of DNA binding employed by SIP1 can be generalized to other zinc finger containing Smad-interacting proteins, and represents a common feature of several Smad partners in the nucleus.

These results demonstrate a novel mode of DNA binding for δEF1 family of transcription factors. This mode of DNA binding is also relevant to other families of transcription factor that contains separated clusters of zinc fingers.

Materials and Methods

Plasmid Constructions.

For expression in mammalian cells, the SIP1 (34) and δEF1 (5) cDNAs were subcloned into pCS3 (27). In this plasmid, the SIP1 and δEF1 open reading frames are fused to a (Myc)$_6$ tag at the N-terminus. SIP1 cDNA was also cloned into pCDNA3 (Invitrogen) as an N-terminal fusion with the FLAG tag. For the expression of SIP1$_{NZF}$ and SIP1$_{CZF}$, we sub-cloned into pCS3 the cDNA fragments encoding amino acids 1 to 389 and 977 to 1214, respectively. SIP1$_{CZF}$ (as amino acids 957 to 1156) and SIP1$_{NZF}$ (amino acids 90 to 383) were also produced in *E. coli* as a GST fusion protein (in pGEX-5x-1, Pharmacia) and purified using the GST purification module (Pharmacia). Identical mutations to those made in AREB6 (10) were also introduced in the SIP1 zinc fingers. Mutagenesis of zinc fingers NZF3, NZF4, CZF2 and CZF3 involved substitution of their third His to a Ser. These mutations were introduced using a PCR based approach with the following primers:

SIP1$_{NZF3Mut}$,
5'-CCACCTGAAAGAA<u>TC</u>CCTGAGAATTCACAG; (SEQ ID NO:6)

SIP1$_{NZF4Mut}$,
5'-GGGTCCTACAGTTCA<u>TC</u>TATCAGCAGCAAG; (SEQ ID NO:7)

SIP1$_{CZF2Mut}$,
5'-CACCACCTTATCGAGT<u>CC</u>TCGAGGCTGCAC; (SEQ ID NO:8)

SIP1$_{CZF3Mut}$,
5'-TCCTACTCGCAGT<u>CC</u>CATGAATCACAGGTAC. (SEQ ID NO:9)

The respective mutated clusters were re-cloned in full size SIP1 in pCS3 in order to produce in mammalian cells the mutated SIP1 proteins named NZF3mut, NZF4mut, CZF2mut and CZF3mut, respectively. Furthermore, these mutated clusters were sub-cloned into pGEX5-X2 (Pharmacia), and produced in *E. coli* as a GST fusion protein (GST-NZF3mut, GST-NZF4mut, GST-CZF2mut and GST-CZF3mut). All constructs were confirmed by restriction mapping and sequencing.

Cell Culture and DNA Transfection.

COS1 cells were grown in DMEM supplemented with 10% fetal bovine serum. Cells were transfected using Fugene according to the manufacturer's protocol (Boehringer Mannheim), and collected 30 to 48 hours after transfection.

Gel Retardation Assay.

The Xbra-WT oligonucleotide covers the region from −344 to −294 of the Xbra2 promoter (16). The region between −412 to −352 of the α4-integrin promoter is present within the α4I-WT oligonucleotide (26). The Ecad-WT probe contains the region between −86 to −17 of the human Ecad promoter (2). The sequences of the upper strand of the wild types and mutated double-stranded probes are listed in Table 1. Double-stranded oligonucleotides were labeled with [$^{32}$P]-γ-ATP and T4 polynucleotide kinase (New England Biolabs). Total cell extracts were prepared from COS1 cells (25) transfected with different pCS3 vectors allowing synthesis of full length SIP1, full length δEF1, and different mutant forms of SIP1 (25), or co-production of equal amounts of Myc-tagged SP1 and FLAG-tagged SIP1. GST-SIP1 fusion proteins were purified from *E. coli* extract using the GST purification module (Pharmacia), and tested in gel retardation. The DNA binding assay (20 μl) was performed at 25° C., with 1 μg of COS1 total cell protein, 1 μg of poly dI-dC, 10 pg of $^{32}$P-labeled double-stranded oligonucleotide (approx. 10$^4$ Cerenkov counts) in the δEF1 binding buffer described previously (30). For supershift experiments, the extracts were incubated with anti-Myc (Santa Cruz) or anti-FLAG (Kodak) antibodies. For competition, an excess of unlabeled double-stranded oligonucleotides was added together with the labeled probe. The binding reaction was loaded onto a 4% polyacrylamide gel (acrylamide/bis-acrylamide, 19:1) prepared in 0.5×TBE buffer. Following electrophoresis, gels were dried, and exposed to X-Ray film. All experiments were repeated at least three times.

Methylation Interference Assay.

The upper and the lower strands of the Xbra-WT probe were labeled separately and annealed with excess of complementary DNA strand. The probes were precipitated and treated with di-methyl-sulfate (8). The methylated probe (10$^5$ Cerenkov counts) was incubated in a 10× gel retardation reaction (see above) (200 μl final volume) with 10 μg of total cell extract from COS1 cells expressing either SIP1$_{FS}$ or SIP1$_{CZF}$. After 20 minutes of incubation at 25° C., the products were loaded onto a 4% polyacrylamide gel, and electrophoresis was performed as for the gel retardation assay. Subsequently, the gel was blotted onto DEAE-cellulose membrane; the transfer was performed at 100 V for 30 minutes in 0.5×TBE buffer. The membrane was then exposed for one hour, and the bands corresponding to the SIP1$_{FS}$ (or SIP1$_{CZF}$) and the free probe were eluted at 65° C., using high salt conditions (1M NaCl, 20 mM Tris, pH 7.5, 1 mM EDTA). The eluted DNA was precipitated and treated with piperidine (18). After several cycles of solubilization in water and evaporation of the liquid under vacuum, the resulting DNA pellet was dissolved in 10 μl of sequencing buffer (97.5% de-ionized formamide, 0.3% each bromophenol blue and xylene cyanol, 10 mM EDTA) and denatured for five minutes at 85° C. The same amount of counts (1,500 Cerenkov counts) for the free probe and the bound probe was loaded onto a 20% polyacrylamide-8M urea sequencing gel. The gel was run in 0.5×TBE for one hour at 2,000 V. Thereafter, the gel was fixed in 50% methanol/10% acetic acid and dried. The gel was then exposed for autoradiography.

Western Blot Analysis.

Transfected cells were washed with PBS-O (137 mM NaCl, 2.7 mM KCl, 6.5 mM Na$_2$HPO$_4$, 1.5 mM KH$_2$PO$_4$), collected in detachment buffer (10 mM Tris pH 7.5, 1 mM EDTA, 10% glycerol, with protease inhibitors (Protease inhibitor Cocktail tablets, Boehringer Mannheim)) and pelleted by low spin centrifugation. The cells were then solubilized in 10 mM Tris, pH 7.4, 125 mM NaCl, 1% Triton X-100. For direct electrophoretic analysis, gel sample buffer was added to the cell lysates and the samples were boiled. For other experiments, lysates were first subjected to immunoprecipitation with either anti-Myc or anti-FLAG antibodies. Antibodies were added to aliquots of the cell lysates, which were incubated overnight at 4° C. The antibodies and the bound protein(s) of the cell lysate were coupled as a complex to protein A-Sepharose for two hours at 4° C. The immunoprecipitates were washed four times in NET buffer (50 mM Tris pH 8.0, 150 mM NaCl, 0.1% NP40, 1 mM EDTA, 0.25% gelatin), resolved by SDS-polyacrylamide (7.5%) gel electrophoresis, and electrophoretically transferred to nitrocellulose membranes. Membranes were blocked for two hours in TBST (10 mM Tris pH 7.5, 150 mM NaCl, 0.1% TWEEN-20) containing 3% (w/v) non-fat milk, and incubated with primary antibody (1 μg/ml) for two hours, followed by secondary antibody (0.5 μg/ml) linked to horseradish peroxidase. Immunoreactive bands were detected with an enhanced chemiluminescence reagent (NEN).

*Xenopus laevis* Transgenesis and Whole-Mount in Situ Hybridization

*Xenopus* embryos transgenic for Xbra2-GFP were generated as described previously (Kroll and Amaya, 1996), with the following modifications. A Drummond Nanoinject was used for injecting a fixed volume of 5 nl of sperm nuclei suspension per egg, at a theoretical concentration of two nuclei per 5 nl. NotI was used for plasmid linearization and nicking of sperm nuclei. Approximately 800 eggs were injected per egg extract incubation. The procedure resulted in a successful cleavage of the embryo with rates between 10% and 30%. Of these, 50 to 80% completed gastrulation, and 20 to 30% developed further into normal swimming tadpoles, if allowed. The transgenic frequency, as analyzed by expression, varied between 50 to 90%. Embryos were staged according to Niewkoop and Faber (1967). A minimum of 30 expressing embryos were analyzed per construct and shown stage. Whole-mount in situ hybridization for the GFP reporter gene was as described previously (Latinkic et al., 1997). After color detection, embryos were dehydrated and cleared in a 2:1 mixture of benzyl alcohol/benzyl benzoate.

Table 1 lists the probes used herein. (See also, the Sequence Listing, which is incorporated herein.) The "Spacing" column is the number of nucleotides present between two CACCT (SEQ ID NO:1) sequences. In the corresponding Table 1 of the incorporated parent PCT International Patent application, the CACCT (SEQ ID NO:1) sequences are highlighted in bold. In that Table, the underlined gaps correspond to deletions of nucleotides from the wild-type probes. For some probes, only the residues that were changed in comparison to the wild-type probes were indicated in order to facilitate interpretation of the introduced mutations.

TABLE 1

| OLIGO | SEQUENCE | SPACING |
|---|---|---|
| Xbra-WT | SEQ ID NO: 10 | 24 |
| Xbra-D | SEQ ID NO: 11 | |
| Xbra-E | SEQ ID NO: 12 | |
| Xbra-F | SEQ ID NO: 13 | |
| Rdm + Xbra-E | SEQ ID NO: 14 | |
| Xbra-F + AREB6 | SEQ ID NO: 15 | 23 |
| Rdm + AREB6 | SEQ ID NO: 16 | |
| Xbra-J | SEQ ID NO: 17 | |
| Xbra-K | SEQ ID NO: 18 | |
| Xbra-L | SEQ ID NO: 19 | |
| Xbra-M | SEQ ID NO: 20 | |
| Xbra-N | SEQ ID NO: 21 | |
| Xbra-O | SEQ ID NO: 22 | |
| Xbra-P | SEQ ID NO: 23 | |
| Xbra-Q | SEQ ID NO: 24 | |
| Xbra-R | SEQ ID NO: 25 | |
| Xbra-S | SEQ ID NO: 26 | |
| Xbra-Z | SEQ ID NO: 27 | |
| Xbra-B | SEQ ID NO: 28 | 21 |
| Xbra-C | SEQ ID NO: 29 | 21 |
| Xbra-U | SEQ ID NO: 30 | 14 |
| Xbra-EE | SEQ ID NO: 31 | 18 |
| Xbra-ErE | SEQ ID NO: 32 | 20 |
| Xbra-FrF | SEQ ID NO: 33 | 24 |
| Xbra-V | SEQ ID NO: 34 | 24 |
| Xbra-W | SEQ ID NO: 35 | 24 |
| α4I-WT | SEQ ID NO: 36 | 34 |
| α4I-A | SEQ ID NO: 37 | |
| α4I-B | SEQ ID NO: 38 | |
| Ecad-WT | SEQ ID NO: 39 | 44 |
| Ecad-A | SEQ ID NO: 40 | |
| Ecad-B | SEQ ID NO: 41 | |

Further Materials and Methods:

Gel retardation assay with different probes from the Xbra2 promoter: The different Xbra $^{32}$P labeled probes (10 pg) were incubated with 1 μg of total protein extract from COS1 cells transfected with pCS3-SIP1$_{CZF}$, with pCS3-SIP1$_{FS}$ or from mock-transfected cells.

Two CACCT (SEQ ID NO:1) sites are contacted upon binding of SIP1$_{FS}$ to the Xbra2 promoter: Only mutations within the upstream CACCT (SEQ ID NO:1) sequence (as revealed by scanning mutagenesis, see Table I) or the downstream CACCT (SEQ ID NO:1) sequence of Xbra-WT abolish SIP1$_{FS}$ binding. Methylation interference assay indicates that SIP1$_{FS}$ contacts both CACCT (SEQ ID NO:1) sequences. Xbra-WT either labeled in the upper or the lower strand were methylated and incubated with total extract from COS1 cells transfected either with pCS3-SIP1$_{FS}$ or pCS3-SIP1$_{CZF}$. The DNA retarded in the shifted complex or the unbound DNA (FREE) were purified, cleaved with piperidine and run onto a sequencing gel. Guanine residues are methylated in the free probe. The upstream and the downstream CACCT (SEQ ID NO:1) from the Xbra2 promoter are indicated.

Two CACCT (SEQ ID NO:1) sequences are necessary for the binding of SIP1$_{FS}$ and δEF1 to the Xbra2, the α4-integrin and the E-cadherin promoters: δEF1 binding to the Xbra2 promoter; SIP1 and δEF1 binding to the α4-integrin promoter; binding of SIP1 and δEF1 to the α4-integrin promoter, including competition with excess of non-labeled wild-type and mutated binding sites; binding of SIP1 and δEF1 to the E-cadherin promoter. In each binding reaction, 10 pg of labeled probes were incubated with 1 μg of a total cell protein extract prepared from COS1 cells transfected with either pCS3SIP1$_{FS}$ or pCS3-δEF1. In the competition experiments, 5 ng and 50 ng of unlabeled DNA were added at the same time as the labeled probe. Myc-tag directed antibody was added to the binding reaction and the supershifted complex. δEF1 and the SIP1 retarded complexes were demonstrated. For the sequences of all probes, see Table 1 and the sequence listing.

The spacing and the relative orientation of the CACCT (SEQ ID NO:1) sequences are not critical for the binding of SIP1$_{FS}$ and δEF1 to the Xbra2 promoter: Ten pg of labeled probes were incubated with 1 μg of a total cell protein extract prepared from COS1 cells transfected with either pCS3-SIP1$_{FS}$ or pCS3-δEF1. We used 10 pg of the Xbra-E probe and 10 pg of the Xbra-F probe in the same binding reaction. For reasons of clear and comparative presentation, we omitted the free probe from the SIP1 binding reactions.

The integrity of both SIP1 zinc finger clusters is necessary for the binding of SIP1$_{FS}$ to DNA: Mutations within NZF3, NZF4, CZF2, CZF3 abolish the DNA-binding activity of either the SIP1$_{NZF}$ or SIP1$_{CZF}$ zinc finger clusters. The wild-type and mutated zinc finger clusters were fused to GST and the fusion proteins were produced in E. coli. After purification, an equal amount of each fusion proteins (0.1 ng) was incubated with 10 pg of labeled Xbra-E probe. Mutations within NZF3, NZF4, CZF2 or CZF3 affect the binding of SIP1$_{FS}$ to the Xbra-WT probe. Ten pg of labeled Xbra-WT probe were incubated with 1 μg of a total cell protein extract prepared from COS1 cells transfected with either pCS3-SIP1$_{FS}$, pCS3-SIP1$_{NZF3mut}$, pCS3-SIP1$_{NZF4mut}$, pCS3-SIP1$_{CZF2mut}$ or pCS3-SIP1$_{CZF3mut}$. All possible combinations of two COS cell extracts (1 μg of each) expressing different of SIP1 mutants were tested. Myc-tag directed antibody was added to the binding reaction and the supershifted complex and the SIP1$_{FS}$ retarded complex are indicated. Mutations within NZF3, NZF4, CZF2 or CZF3 abolish the binding of SIP1$_{FS}$ to the α4-integrin promoter. Ten pg of labeled α4I-WT probe were incubated with 1 μg of a total cell protein extract prepared from COS1 cells transfected with either pCS3-SIP1$_{FS}$, pCS3-SIP1$_{NZF3mut}$, pCS3-SIP1$_{NZF4mut}$, pCS3-SIP1$_{CZF2mut}$, or pCS3-SIP1$_{CZF3mut}$. Myc-tag directed antibodies were added to the binding reaction and the supershifted complex and the SIP1$_{FS}$ retarded complex are indicated. SIP1 mutants are produced in comparable amounts in COS cells. Ten μg of the COS cell total extract were analyzed by Western blotting using the anti-Myc antibody. SIP1 mutant expression levels are in fact slightly higher that SIP1-WT expression level.

SIP1$_{FS}$ binds as a monomer to the Xbra-WT probe.

10 pg of labeled Xbra-WT probe were incubated with 1 μg of total cell protein prepared from COS1 cells transfected with an equal amount of pCS3-SIP1$_{FS}$ (Myc-tagged) and of pCDNA3-SIP1 (Flag-tagged). Anti-Flag and anti-Myc antibodies were added separately or both anti-Flag and anti-Myc antibodies were added to the binding assay. The Flag- and the Myc-supershifted complexes are indicated.

The integrity of CZF or NZF is necessary for SIP1 repressor activity.

SIP1$_{FS}$ binding to a gel-purified fragment derived from the multiple CACCT-containing artificial promoter from reporter plasmid p3TP-Lux. Anti-Myc tag antibody was added; the supershifted complex is indicated. Co-transfection assay of pCS3-SIP1$_{FS}$, pCS3-CZF3-Mut or pCS3-NZF3-Mut together with the p3TP-Lux reporter vector is conducted. The activity is expressed in percentage of full SIP1$_{FS}$ repressor activity, which is 100%.

Ectopic activity of the mutated Xbra2 promoter variants (Xbra2-Mut) in transgenic frog embryos: SIP1$_{FS}$ binding to the wild-type and mutated Xbra2 promoter elements. Whole-mount in situ hybridization for GFP mRNA of Xenopus embryos transgenic for a wild-type or point-mutated 2.1 kb Xbra2 promoter fragment driving a GFP reporter. All embryos were fixed at stage 11 and cleared for better visualization of the signal. Percentages are indicative of intermediary phenotype (i.e., 35% of transgenic embryos displayed the normal Xbra2 expression pattern and 65% showed ectopic expression) has a structure similar to ä-EF1 has a structure similar to ä-EF1 has a structure similar to ä-EF1 has a structure similar to ä-EF1 has a structure similar to ä-EF1 has a structure similar to ä-EF1 has a structure similar to ä-EF1 has a structure similar to ä-EF1 has a structure similar to ä-EF1 has a structure similar to ä-EF1 has a structure similar to ä-EF1.

SIP1 was recently isolated as a Smad-binding protein. It binds Smad1, Smad5 and Smad2 in a ligand-dependent fashion (in BMP and activin pathways) (34). SIP1 is a new member of the family of two-handed zinc finger/homeodomain transcription factors, which includes vertebrate δEF1 and Drosophila Zfh-1 (4, 5). Like these, SIP1 contains two widely separated zinc finger clusters. One cluster of four zinc fingers (three CCHH and one CCHC fingers) is located at the protein's N-terminal region and another cluster of three CCHH zinc fingers is present at the C-terminal region (FIG. 1A). Between SIP1 and δEF1, a high degree of sequence identity is apparent within the N-terminal zinc finger cluster (87%), and the C-terminal zinc finger cluster (97%) (see, FIG. 1B), whereas the two proteins are less conserved in the regions outside the zinc finger clusters (34). Therefore, we assumed that SIP1 and δEF1 would bind to very similar sequences. In addition, the N-terminal and C-terminal zinc finger clusters of δEF1 bind to very similar sequences, which contain the core CACCT (SEQ ID NO:1) consensus sequence (10). Within the N-terminal cluster, both δEF1$_{NZF3}$ and δEF1$_{NZF4}$ are the main determinants for binding to the CACCT (SEQ ID NO:1) consensus sequence, and 8EF1$_{CZF2}$ and δEF1$_{CZF3}$ are required for the binding of the C-terminal cluster (10). Moreover, the δEF1$_{NZF3+NZF4}$ domain shows high homology (67%) with the δEF1$_{CZF2+CZF3}$ domain and this may explain why these two clusters bind to similar consensus target sites on DNA (FIG. 1C). All the residues essential for binding, and which are conserved between δEF1$_{NZF3+NZF4}$ and δ EF1$_{CZF2+CZF3}$, are also conserved between SIP1$_{NZF3+NZF4}$ and SIP1$_{CZF2+CZF3}$. Taken together, these comparisons suggest that the N- and C-terminal zinc finger clusters of SIP1 would also bind to very similar target sequences.

Two CACCT (SEQ ID NO:1) sites are necessary for the binding of SIP1 to the Xbra2 promoter. CACCT sites are necessary for the binding of SIP1 to the Xbra2 promoter CACCT sites are necessary for the binding of SIP1 to the Xbra2 promoter CACCT sites are necessary for the binding of SIP1 to the Xbra2 promoter CACCT sites are necessary for the binding of SIP1 to the Xbra2 promoter SIP1 binds to the Xenopus Xbra2 promoter and represses expression of Xbra2 mRNA when overexpressed in the Xenopus embryo (34). The Xbra2 promoter contains several CACCT (SEQ ID NO:1) sequences, two of which are localized in a region (−381 to −231) necessary for the induction by activin (16). These two sites, an upstream CACCT (SEQ ID NO:1) and a downstream AGGTG (SEQ ID NO:3) (i.e., 5'-CACCT (SEQ ID NO:1) on the other DNA strand) respectively, are separated by 24 bp. To further elucidate the binding requirements of SIP1 to these sites, a corresponding 50 bp-long oligonucleotide (Xbra-WT) was used as a probe in electrophoretic mobility shift assays (EMSAs). The Xbra-D probe, that contains a mutation of the downstream AGGTG (SEQ ID NO:3) site to AG<u>A</u>TG, was included also. A similar mutation was previously shown to abolish the binding of δEF1 to the κE2 enhancer (30). In addition, we also tested the downstream site (probe Xbra-E) and the upstream site (probe Xbra-F) independently as shorter probes. These probes were incubated with total extracts of COS cells expressing the Myc-tagged C-terminal zinc finger cluster of SIP1 ($SIP1_{CZF}$), the Myc-tagged N-terminal zinc finger cluster of SIP1 ($SIP1_{NZF}$), or Myc-tagged full size SIP1 ($SIP1_{FS}$).

When mock-transfected COS cells are used as control with the A probe, two weak complexes and one strong complex are visualized. Using competitor oligonucleotides, the two weak complexes turned out to be non-specific, whereas the strong, fast migrating complex shows specificity for binding to the Xbra probe. The latter observation suggests that COS cells contain an endogenous protein that can bind to the Xbra-WT probe. When $SIP1_{CZF}$ is present in the extract, we observed a strong and slow migrating complex, in addition to the endogenous binding activity from the COS extract. This complex could be supershifted with an anti-Myc antibody, which confirms that it results from binding of $SIP1_{CZF}$ to the Xbra-WT probe. Mutation of the downstream site (Xbra-D probe) strongly affected the formation of this $SIP1_{CZF}$ complex. Moreover, $SIP1_{CZF}$ binds to the Xbra-E probe, but not to the Xbra-F probe indicating that the downstream site is essential for binding of $SIP1_{CZF}$, and $SIP1_{CZF}$ may exclusively bind to this site. The strong complex visualized with the Xbra-F probe was also present in $SIP1_{FS}$ extracts and in mock extract, and originates from hitherto uncharacterized endogenous COS cells protein binding to the Xbra-F probe. In addition, COS cell extracts containing $SIP1_{NZF}$ displayed similar binding patterns in EMSAs as obtained with $SIP1_{CZF}$. It is apparent that, like in δEF1 (10), both zinc finger clusters of SIP1 have similar DNA binding features.

A strong complex, corresponding to $SIP1_{FS}$, is also generated with the Xbra-WT probe. It should be noted that the $SIP1_{CZF}$ production level in COS cells is approximately 50-fold higher than the $SIP1_{FS}$ level. For each EMSA reaction, we used the same amount of crude COS cell proteins. The binding of $SIP1_{FS}$ to Xbra-WT probe is as strong as the binding of $SIP1_{CZF}$. Interestingly, this indicates that the affinity of $SIP1_{FS}$ for Xbra-WT is at least 50 times higher than this of $SIP1_{CZF}$.

The $SIP1_{FS}$ complex, similar to $SIP1_{CZF}$ and $SIP1_{NZF}$, is absent when using the mutated Xbra-D probe. Thus, an intact downstream site is again required for the binding of $SIP1_{FS}$. In contrast to $SIP1_{CZF}$ and $SIP1_{NZF}$, which bind with similar affinities to the Xbra-WT and Xbra-E probes, $SIP1_{FS}$ does not bind to the Xbra-E probe. Like $SIP1_{CZF}$ and $SIP1_{NZF}$, $SIP1_{FS}$ does not bind to the Xbra-F probe. We conclude that the downstream site (AGGTG(SEQ ID NO:3)) is necessary for $SIP1_{FS}$ to bind to the Xbra2 promoter. However, this site is not sufficient because additional sequences upstream of the Xbra-E probe are necessary for the binding of $SIP1_{FS}$. One of the reasons for which $SIP1_{FS}$ was unable to bind to the Xbra-E probe may simply be the length of the Xbra-E probe, because it is shorter than the Xbra-WT probe. To test this, we prepared a probe containing a random sequence (Rdm) upstream of the Xbra-E probe (Table 1) in order to extend it to the same length as Xbra-WT. In contrast to $SIP1_{CZF}$, which bound efficiently to Rdm+Xbra-E probe, $SIP1_{FS}$ was unable to bind. This result demonstrates that length of the Xbra-E probe per se is not the cause of the failure of $SIP1_{FS}$ to bind to this probe.

To substantiate that the Xbra-F oligonucleotide also contains sequences necessary for the binding of $SIP1_{FS}$. We fused this oligonucleotide as well as a random sequence upstream of another CACCT (SEQ ID NO:1) site known to be bound strongly by AREB6 protein (Ref. 10) (probes Xbra-F+AREB6 and Rdm+AREB6, respectively). $SIP1_{CZF}$ binds, with equal affinity, both the Xbra-F+AREB6 and Rdm+AREB6 probes indicating that the AREB6 sequence is also recognized by $SIP1_{CZF}$. However, $SIP1_{FS}$ only binds to the Xbra-F+AREB6 probe but not to Rdm+AREB6. This observation confirms that the Xbra-F oligonucleotide contains sequences necessary for the binding of $SIP1_{FS}$. In addition, the only common feature between the Xbra-E and the AREB6 probe is the CAGGTGT sequence, suggesting that no other sequences than this CAGGTGT in the Xbra-E probe are necessary for the binding of $SIP1_{FS}$.

One of the reasons why $SIP1_{FS}$ is unable to bind to the Xbra-E probe might be because the length of the Xbra-E probe is shorter than the length of the Xbra-WT probe. To test this hypothesis, we prepared a probe containing a random sequence upstream of the Xbra-E probe to obtain the same length as the Xbra-WT probe. In contrast to $SIP1_{CZF}$ that binds efficiently to this probe, $SIP1_{FS}$ was unable to bind. This result shows that the Xbra-E probe's length was not the reason why $SIP1_{FS}$ does not bind this probe. To substantiate that the Xbra-F oligonucleotide also contains sequences necessary for the binding of $SIP1_{FS}$, we fused that oligonucleotide and a random sequence upstream of another CACCT (SEQ ID NO:1) site known to bind strongly AREB6 protein (Xbra-F+AREB6 and Rdm+AREB6, respectively). We observed that $SIP1_{CZF}$ binds (with equal affinity) to both the Xbra-F+AREB6 and Rdm+AREB6 probes, indicating that the AREB6 sequence is also recognized by $SIP1_{CZF}$. However, SIP1FS only binds to the Xbra-F+AREB6 probe and not to the Rdm+AREB6 probe. This confirms that the Xbra-F oligonucleotide contains sequences necessary for the binding of $SIP1_{FS}$. In addition, the only common denominator between the Xbra-E and the AREB6 probe is the AGGTG (SEQ ID NO:3) sequence, suggesting that no other sequences than this AGGTG (SEQ ID NO:3) in the Xbra-E probe is necessary for the binding of $SIP1_{FS}$.

To map the sequences within Xbra-F that, in conjunction with the Xbra-E sequence, are required for the binding of $SIP1_{FS}$, we prepared a series of probes, identical in length to Xbra-WT, containing adjacent triple mutations within the Xbra-F part (see, Table 1). Only three of these mutated probes (i.e., Xbra-L, Xbra-M and Xbra-N) affected the binding of $SIP1_{FS}$. Indeed, the upstream CACCT (SEQ ID NO:1) sequence, which is intact in the Xbra-F probe, was modified in the L, M and N probes. We also showed that $SIP1_{FS}$ does not bind to the Xbra-S probe, which contains a point mutation, changing the upstream CA<u>C</u>CT (SEQ ID NO:1) into CA<u>T</u>CT. This mutation is similar to the downstream AG<u>A</u>TG mutation made within the Xbra-D probe.

The results described above are indicative for $SIP1_{FS}$ contacting both CACCT (SEQ ID NO:1) sequences in the Xbra promoter. To further investigate the importance of these sites, a DNA methylation interference assay was carried out. The methylation of three Gs of the downstream AGGTG (SEQ ID NO:3) ($SIP_{DO}$) and of the two Gs of the upstream CACCT (SEQ ID NO:1) ($SIP_{UP}$) was significantly lower in the $SIP1_{FS}$ bound versus unbound probe, suggesting that the methylation of these Gs interfered with the binding of $SIP1_{FS}$. This finding strongly supports that these residues are essential for $SIP1_{FS}$ binding. It has also been observed that the methylation of one of the two Gs localized very close to the $SIP_{DO}$ also interfered with the binding of $SIP1_{FS}$. Consequently it has thus been shown that for $SIP1_{FS}$ two CACCT (SEQ ID NO:1) sequences and their integrity are required for DNA binding.

SIP1 and δEF1 require two CACCT (SEQ ID NO:1) sequences for binding to different potential candidate sites SIP1 and δEF1 have a very similar structure with two very highly conserved zinc finger clusters and it is likely that these two proteins bind DNA in a similar way. We set out to determine whether δEF1 also binds to the Xbra2 promoter by contacting both CACCT (SEQ ID NO:1) sequences. Myc-tagged δEF1 was expressed in COS cells and the corresponding nuclear extracts were tested in EMSA with WT and a panel of mutated Xbra probes. δEF1 binds strongly to the Xbra-WT probe that contains both CACCT (SEQ ID NO:1) sites. However, like SIP1$_{FS}$, δEF1 binds neither the Xbra-E probe comprising only the downstream CACCT (SEQ ID NO:1) site nor the Xbra-F probe containing only the upstream CACCT (SEQ ID NO:1) site. In addition, the point mutation of either the upstream CACCT (SEQ ID NO:1) (Xbra-S) or the downstream CACCT (SEQ ID NO:1) site (Xbra-D) also abolished the binding of δEF1. Therefore, like SIP1$_{FS}$, full length δEF1 requires also the integrity of both CACCT (SEQ ID NO:1) sequences for binding to the Xbra2 promoter. The fact that two CACCT (SEQ ID NO:1) sites are required for the binding of SIP1$_{FS}$ as well as δEF1 may be unique for the Xbra2 promoter. Therefore, the next question was to analyze whether two CACCT (SEQ ID NO:1) sequences are also necessary for SIP1/δEF1 for binding to other target sites. Putative δEF1 and SIP1 binding elements are present in several promoters. One putative δEF1 binding element, indeed containing two intact and spaced CACCT (SEQ ID NO:1) sites, was found within the promoter of the human α4-integrin gene (23). Interestingly, both sites are contained within of E2 boxes. Mutation of these two CACCT sites led to the de-repression of the α4-integrin gene expression in myoblasts, suggesting that δEF1 is a repressor of α4-integrin gene transcription (23). Since these two CACCT (SEQ ID NO:1) sites are closely positioned in the promoter (spacing is 34 bp), we investigated whether both CACCT (SEQ ID NO:1) sequences are required for the binding of δEF1. For this purpose, a 60 bp-long probe overlapping both CACCT (SEQ ID NO:1) sites of the α4-integrin promoter was synthesized (α4I-WT) as well as two mutated versions, i.e., having a point mutation in either the upstream (α4I-B) or the downstream CACCT (SEQ ID NO:1) site (α4I-A), respectively (see Table 1). These probes were tested for binding in EMSAs with COS cell extracts of either δEF1 or SIP1$_{FS}$ transfected cells. Both δEF1 and SIP1$_{FS}$ form strong complexes with the α4I-WT probe. The δEF1 complex was entirely supershifted with an anti-Myc antibody, demonstrating its specificity. Both the binding of SIP1 and of δEF1 is abolished or strongly affected by a mutation of either the upstream or the downstream CACCT (SEQ ID NO:1) site. Moreover, competition experiments revealed that 50 ng of unlabeled α4I-WT probe was sufficient to abolish the binding of SIP1 or δEF1 to the α4I-WT probe, whereas 50 ng of either unlabeled α4I-A or α4I-B probes were not. We concluded that both SIP1$_{FS}$ and δEF1 require the integrity of two CACCT (SEQ ID NO:1) sites for binding to the promoter of the α4-integrin gene.

We also found two closely positioned CACCT (SEQ ID NO:1) sites within the promoter of the human E-cadherin gene. An oligonucleotide comprising both CACCT (SEQ ID NO:1) sites of this E-cadherin promoter was used as a probe (Ecad-WT) together with SIP1$_{FS}$ or δEF1 extracts in EMSAs. Both SIP1$_{FS}$ as well as δEF1 form a complex with this probe. However, when either the upstream (Ecad-A probe) or the downstream (Ecad-B probe) CACCT (SEQ ID NO:1) site was mutated, the binding of SIP1$_{FS}$ and δEF1 was abolished. This finding also suggests that the two CACCT (SEQ ID NO:1) sites in this promoter represent a high affinity site for the binding of two-handed zinc finger/homeodomain transcription factors.

From the alignment of the Xbra-WT, α4I-WT and Ecad-WT probes (see Table 1) we observed no obvious homology, except for one CACCTG (SEQ ID NO:2) site and a second CACCT (SEQ ID NO:1) site. Our results described herein and this alignment indicate that only those sequences participating in the binding of either SIP1$_{FS}$ or δEF1. We therefore conclude that for binding to target promoters, SIP1$_{FS}$ or δEF1 require at least one CACCT (SEQ ID NO:1) site and one CACCTG (SEQ ID NO:2) site.

Spacing variations and orientation of the CACCT (SEQ ID NO:1) sites: Within the Xbra-WT, α4I-WT and Ecad-WT probes (Table 1), the spacing between the two CACCT (SEQ ID NO:1) sequences was 24, 34, and 44 bp, respectively. Since SIP1$_{FS}$ and δEF1 bind efficiently to these probes, this demonstrates that these proteins can accommodate spacing between the two CACCT (SEQ ID NO:1) sites ranging from 24 bp to at least 44 bp. To further investigate whether the spacing between the two CACCT (SEQ ID NO:1) sites is an important parameter for binding, we generated different Xbra probes with deletions between these sites. Two mutant probes (Xbra-B and Xbra-C) have a deletion of three adenines whereas probe Xbra-U has a deletion of ten nucleotides. These probes were tested in EMSA with cell extracts from COS cells expressing either SIP1$_{FS}$ or δEF1. Both SIP1$_{FS}$ and δEF1 bind with equal affinity to the Xbra-WT, Xbra-B, Xbra-C and Xbra-U probes. As already suggested by the results shown for different promoters, this indicates that also within the same promoter element, the spacing between the two CACCT (SEQ ID NO:1) sites is not a critical parameter for the binding of these two transcription factors.

By extensive comparison of the Xbra-WT, α4I-WT and Ecad-WT probes, we observed that in the case of the Xbra-WT and α4I-WT probes, the orientation of the two CACCT (SEQ ID NO:1) sites is CACCT-N-AGGTG (SEQ ID NO:1 and SEQ ID NO:3 separated by N), whereas in Ecad-WT the orientation is AGGTG-N-CACCT (SEQ ID NO:3 and SEQ ID NO:1 separated by N). Because of the non-palindromic feature of the CACCT (SEQ ID NO:1) site, these two sites could be assumed substantially different. However, SIP1$_{FS}$ and δEF1 bind to these differently oriented sites with comparable affinities suggesting that SIP1$_{FS}$ and δEF1 can bind irrespective of the orientation of the two CACCT (SEQ ID NO:1) sites.

To further investigate the orientation of the two CACCT (SEQ ID NO:1) sites with respect to the DNA binding capacity of SIP1$_{FS}$ and δEF1, additional probes were designed. Probe Xbra-EE contained a tandem repeat of the Xbra-E probe, whereas probe Xbra-ErE contained an inverted repeat of the same Xbra-E sequence. In addition, we synthesized Xbra-V, in which the upstream CACCT (SEQ ID NO:1) site (plus one extra base pair on each side) was replaced by the downstream AGGTG (SEQ ID NO:3) sequence and vice versa. Finally, in the Xbra-W probe, only the downstream site was replaced by the upstream CACCT (SEQ ID NO:1) sequence. All these probes were again tested in EMSAs with extracts prepared from COS cells expressing either SIP1$_{FS}$ or δEF1. We observed the strongest binding of SIP1$_{FS}$ or δEF1 to the Xbra-EE probe. Therefore, SIP1$_{FS}$ and δEF1 cannot bind to Xbra-E, containing a single CACCT (SEQ ID NO:1) site, but bind strongly when this sequence is duplicated, again indicating the requirement of two CACCT (SEQ ID NO:1) sites. In addition, it is evident that these two sites have to be present on the same DNA fragment and not on two separated strands (see, below). SIP1 and δEF1 bind to Xbra-ErE, also suggesting that the respective orientation of the two CACCT (SEQ ID NO:1) sites is not critical for binding. Furthermore, switching both the upstream and the downstream sites (probe Xbra-V) or replacing only the upstream site by a second copy of the downstream site (probe Xbra-W) did not have an effect on SIP1$_{FS}$ and δEF1 binding. From these experiments, we conclude that neither the spacing between the two CACCT (SEQ ID NO:1) sites nor the respective orientation of these two sites is critical for the binding of two-handed zinc finger/homeodomain transcription factors in vitro.

Surprisingly, not all CACCT (SEQ ID NO:1) duplicated sites can bind these factors. In fact, duplication of the Xbra-F sequence, which in combination with the Xbra-E sequence was shown to be necessary for the binding of SIP1$_{FS}$ and δEF1, is refractory to binding of SIP1$_{FS}$ and δEF1. This suggests that the CACCT (SEQ ID NO:1) site within the Xbra-F context is a low affinity site and that sequences adjacent to this CACCT (SEQ ID NO:1) site may optimize the affinity. In addition, the fact that neither the C-terminal cluster nor the N-terminal cluster can bind independently to the Xbra-F probe confirms the assumption that this site displays low affinity. In contrast, the CACCTG (SEQ ID NO:2) site present in the Xbra-E probe can bind SIP1$_{CZF}$ and SIP1$_{NZF}$, and a duplication of this element creates a high affinity-binding site for both SIP1$_{FS}$ and full length δEF1. This suggests that the terminal G base in the downstream site may also allow to discrimination between a high and low affinity-binding site. However, the CACCT (SEQ ID NO:1) site in Xbra-F may only bind one of the zinc finger clusters of SIP1$_{FS}$ once the other cluster has occupied the neighboring high affinity CACCTG (SEQ ID NO:2) site (in Xbra-E). To confirm the importance of the terminal G base residue for the binding of SIP1$_{FS}$ and δEF1, we mutated the downstream CACCTG (SEQ ID NO:2) site to CACCT<u>A</u> (probe Xbra-Z). The binding of SIP1$_{FS}$ or δEF1 to the Xbra-Z probe decreased strongly (compared with the Xbra-WT probe) suggesting that this G-base residue is important for generating a high affinity-binding site for both SIP1$_{FS}$ and δEF1.

Finally, when Xbra-E and Xbra-F probes are mixed before adding SIP1FS or δEF1, no binding is observed, again indicating that both CACCT (SEQ ID NO:1) sites have to be in the cis configuration, i.e., on the same DNA.

SIP1 and δEF1 bind to DNA elements containing two CACCT (SEQ ID NO:1) sites and both of these proteins contain two clusters of zinc fingers capable of binding independently to CACCT (SEQ ID NO:1) sites. In subsequent work, we evaluated the importance of each zinc finger cluster for the binding of SIP1FS to DNA. Mutations destroying either the third or the fourth zinc finger of the N-terminal cluster of δEF1$_{NZF}$ were shown to abolish the binding of this cluster to the DNA. Similarly, mutagenesis of the second or the third zinc finger in the C-terminal cluster also abolished the binding of δEF1$_{CZF}$ to CACCT (SEQ ID NO:1) (10). Therefore, we introduced in the SIP1$_{NZF}$ and SIP1$_{CZF}$ clusters mutations similar to those in δEF1. These mutated and wild-type clusters were fused to GST and the fusions proteins were purified from bacteria. We demonstrate that both wild-type SIP1$_{NZF}$ and SIP1$_{CZF}$ strongly bind to the Xbra-E probe. However, with the same amount of purified mutant cluster/GST fusion proteins (GST-NZF3, GST-NZF4, GST-CZF2 and GST-CZF3), no binding to the Xbra-E probe could be detected with any of these fusion proteins. Indeed, these mutations also abolish the capacity of each cluster (SIP1$_{NZF}$ and SIP1$_{CZF}$) to bind independently to a CACCT (SEQ ID NO:1) site.

We then introduced similar mutations in full size SIP1 (NZF3-Mut, NZF4-Mut, CZF2-Mut and CZF3-Mut), and over-expressed these SIP1 mutants in COS cell as Myc-tagged proteins. The expression of the different mutants was established and normalized by Western blot analysis using anti-Myc antibody. By means of EMSAs, we observed that WT SIP1 binds strongly to the Xbra-WT probe, and that the SIP1-complex is super-shifted upon incubation with an anti-Myc antibody. In contrast, none of the mutant forms of full size SIP1 was able to form a SIP1-like complex or a SIP1 super-shifted complex. The same observations were made when the αI4-WT probe was used as a probe. In conclusion, full size SIP1 requires the binding capacities of both intact zinc fingers clusters to bind to its target, which necessarily contains two CACCT (SEQ ID NO:1) sites. The effect of these mutations on the repressor activity of SIP1 was tested in a transfection assay together using p3TP-Lux reporter plasmid. This plasmid contains three copies, each of which has one CACCT (SEQ ID NO:1), of a sequence covering the −73 to −42 region of human collagenase promoter (de Groot and Kruijer, 1990). SIP1 bound to a fragment containing this multimerized element, but neither NZF3-Mut nor CZF3-Mut was able to bind. Over-expression of SIP1 in CHO cells leads to a strong repression of the p3TP-Lux basal transcriptional activity. However, the repression was six to seven-fold lower upon over-expression of SIP1 mutants defective in DNA binding (NZF3-Mut or CZF3-Mut). Therefore the integrity of both zinc finger clusters is necessary for both the DNA-binding and optimal, i.e., wild-type repressor activity of SIP1.

SIP1 binds to DNA as a monomer: The observation that the integrity of both zinc fingers clusters is required for SIP1 binding to two CACCT (SEQ ID NO:1) sequences, suggests that SIP1 binds as a monomer, in which each zinc finger cluster contacts one such site. However, it can be hypothesized that SIP1 binds its target sites as a dimer implying that one of the SIP1 molecules of the dimer would bind one CACCT (SEQ ID NO:1) site via its N-terminal zinc finger cluster, while the second SIP1 molecule would contact the DNA via its C-terminal zinc finger cluster. Since both zinc finger clusters are necessary for binding, the zinc finger cluster not interacting with the DNA would then be involved in dimerization. Consequently, some combinations of NZF and CZF mutants should generate a dimer configuration that binds DNA. In none of the combinations of NZF and CZF mutations could binding to the Xbra-WT probe be detected. Although we cannot rule out that these mutations also affect potential dimer formation, it is highly unlikely that the same mutation affects both the DNA-binding capacity as well as the protein-protein interaction. Moreover, it is highly unlikely that two different mutants (having different mutations within a cluster) would behave the same.

To address this experimentally, we used a combination of differently tagged SIP1 in supershift experiments in EMSAs. First, we produced Myc-tagged and/or FLAG-tagged SIP1$_{FS}$ separately at comparable levels in COS cells, and confirmed that both proteins bind to DNA with similar affinities. The SIP1 complex generated with Myc-tagged SIP1 has a slightly slower migration than the FLAG-tagged complex (the Myc-tag is longer than the FLAG-tag). Extracts prepared from COS cells expressing similar amounts of both Myc-tagged and FLAG-tagged SIP1 were incubated with the Xbra-WT probe and used in EMSAs. We observed the formation of a broad SIP1 complex that is a combination of both the fast migrating FLAG-tagged SIP1 complex with the slow migrating Myc-tagged SIP1 complex. Using an anti-FLAG antibody, only the lower part of the complex corresponding to FLAG-tagged SIP1 is super-shifted, whereas about 50% of the radioactivity remains within the Myc-tagged SIP1 complex. This indicates that the latter SIP1 complex is not super-shifted with the anti-FLAG antibody. Conversely, incubating the extract with an anti-Myc antibody super-shifted only the lower part of the complex corresponding to Myc-tagged SIP1 whereas 50% of the radioactivity is retained within the FLAG-tagged SIP1 complex. Again, this indicates that no FLAG-tagged SIP1 is super-shifted with an anti-Myc antibody. Using both antibodies, we observed the same two super-shifted bands, which correspond to the Myc-tagged and the FLAG-tagged super-shifted complex, in the upper part of the gel. If SIP1 dimers would be formed, then at least some heterodimers would be assembled from Myc-tagged SIP1 and FLAG-tagged SIP1. However, we detected no other super-shifted band corresponding to a potential double super-shift, viz. super-shifted with both anti-Myc- and anti-FLAG-antibodies. Hence, this experiment gave no detectable dimer formation between FLAG-tagged SIP1 and Myc-tagged SIP1.

Finally, FLAG-tagged SIP1 in a COS cell extract was immunoprecipitated in the presence of a large excess of DNA binding sites. However, co-immunoprecipitation of Myc-tagged SIP1 was not feasible. The reciprocal experiment, i.e., immunoprecipitating with an anti-Myc antibody and detection with an anti-FLAG antibody, did not show any SIP1 dimer either. Taken together, these observations lead us to conclude that SIP1 binds as a monomer to the Xbra-WT probe.

Mutations in either the upstream or downstream CACCT (SEQ ID NO:1) lead to ectopic activity of the Xbra2 promoter in transgenic frog embryos: SIP1 binds to the Xbra2 promoter and represses expression of endogenous Xbra2 mRNA when overexpressed in $Xenopus$ embryos (Verschueren et al., 1999). To analyze the importance of CACCT (SEQ ID NO:1) sequences in the regulation of the Xbra2 promoter in vivo, we tested whether mutations of these would affect Xbra2 promoter activity in transgenic embryos. Xbra2 promoter sequences were fused upstream of the green fluorescent protein (GFP) gene and this reporter cassette was used for transgenesis. A 2.1 kb-long Xbra2 promoter fragment was shown sufficient to yield the reporter protein synthesis in the same domain of the embryo (85% of the embryos, stage 11, n=57) as compared with endogenous Xbra mRNA (which is in the marginal zone) except in the organizer region, for which a regulatory element may be lacking in the reporter cassette tested here.

A single point mutation within the downstream CACCT (SEQ ID NO:1) site in the promoter, which disrupted SIP1 binding (Xbra2-Mut1) and is identical to XbraD, had a severe effect on spatial production of the reporter protein. All embryos showed ectopic expression in the inner ectoderm layer. Mutations within the upstream CACCT (SEQ ID NO:1) sequence (Xbra2-Mut4) also affected the SIP1 binding. We observed in all transgenic embryos (n>30) the same ectopic expression as for the Xbra2-Mut1 mutation. Mutation of the downstream CACCTG (SEQ ID NO:2) to CACCT<u>A</u> (Xbra2-Mut2) also affects SIP1 binding to such probe. This mutation, when introduced into the Xbra2 2.1 kb promoter, also led to ectopic expression of GFP mRNA in all transgenic embryos tested (n>30). We also tested a mutation (Xbra2-Mut3) that decreased by 3 bp the original 24 bp spacing between the two CACCT (SEQ ID NO:1) sequences. This mutation weakened the interaction of such probe with SIP1. This was also reflected in the corresponding transgene embryos (n=37): while 35% of the embryos showed the same expression pattern as the wild-type Xbra2 2.1 kb promoter fragment, 65% had either patches or weak continuous expression in the inner ectoderm layer.

A nice correlation existed between the effect of these mutations on SIP1 binding affinity in EMSA and the phenotype (ectopic expression of the reporter gene) and its penetrance in vivo, indicating the importance of the SIP1 target sites in the normal regulation of Xbra2 expression in $Xenopus$ development (stage 11). It also suggests that a hitherto unknown $Xenopus$ SIP1-like repressor regulates Xbra2 gene expression in vivo. In addition, it confirms that SIP1-like factors require two intact CACCT (SEQ ID NO:1) sites for regulating target promoters like Xbra2.

SIP1 induces invasion by down regulation of E-cadherin: SIP1 binding represses E-cadherin promoter activity through binding on two conserved E-boxes. To elucidate whether SIP1 binding affects the transcriptional activity of the human E-cadherin promoter (−308/+41), we transiently co-expressed full-length SIP1 with E-cadherin promoter driven reporter constructs in the E-cadherin positive cell lines NMe (mouse), MDCK (dog) and MCF7/AZ (human). SIP1 expression led to an 80% decrease of the human E-cadherin promoter activity. To address the binding specificity of SIP1 for the two conserved E-boxes, mutagenesis in either the upstream E-box1 (−75) or downstream E-box3 (−25) or simultaneously in both E-boxes was performed. When co-transfection was performed with SIP1 cDNA and the mutant E-cadherin promoter constructs (68), a de-repression of the human E-cadherin promoter activity was consistently shown. In addition, mutated SIP1 constructs, were co-transfected with the human E-cadherin promoter. Mutation of the N-terminal or C-terminal zinc finger clusters resulted only in a slight derepression of the E-cadherin promoter activity. Interestingly, co-transfection of the human E-cadherin promoter and a SIP1 double mutant, affected in both zinc finger clusters, resulted in a considerable loss of SIP1 mediated repression of E-cadherin promoter activity. We can therefore conclude that SIP1 represses the E-cadherin promoter activity by binding to the two E-boxes and that the two zinc finger clusters are indeed needed for full repression of the E-cadherin promoter activity.

Inducible expression of SIP1 results in dose-dependent loss of E-cadherin protein and mRNA. To elucidate whether SIP1 affects the endogenous E-cadherin expression levels, E-cadherin positive MDCK-Tetoff cells, with high expression of the tTA transactivator was stably transfected with a plasmid expressing a $Myc_6$-tagged full-length mouse SIP1 cDNA under control of a responsive tTA element. To induce SIP1 cells were grown without tetracycline for three days. Analysis of E-cadherin and SIP1 expression by immunofluorescence of a representative cloned transfectant revealed induced SIP1 in the nucleus, concomitant with total loss of the typical honeycomb E-cadherin expression pattern at cell-cell contacts. Western blot analysis confirmed these results. SIP1 induction occurred at tetracycline concentration equal or lower than 2 g/ml. As the tetracycline concentration was gradually decreased, E-cadherin was more strongly repressed and this correlated inversely with SIP1 accumulation. Further, we checked if catenins, linking E-cadherin to the actin cytoskeleton, were influenced by SIP1 expression. Upon a Western blotting, neither αE-catenin nor β-catenin appeared to be affected, and this was confirmed by immunofluorescence. Equal amounts of total RNA of both non-induced and induced cells were analyzed by Northern blotting. After hybridization with an E-cadherin-specific probe, the SIP1 expressing cells showed almost no E-cadherin mRNA expression, whereas the non-induced cells (+tet) expressed normal amounts of E-cadherin mRNA. These results validate those of the reporter assays as induction of SIP1 expression affects endogenous E-cadherin expression through mRNA down-regulation.

SIP1 expression in human carcinoma cell lines: We performed Northern blot analyses to examine the expression of SIP1 in a panel of E-cadherin-negative and -positive cell lines. To avoid possible cross-hybridizations to other members of the δEF1 family, appropriate mouse and human SIP1 cDNA fragments were used as probes. We noted a clear-cut, strong inverse correlation between SIP expression and E-cadherin expression. High expression of SIP1 was found in human fibroblasts and the most prevalent expression of SIP1 was found in E-cadherin-negative carcinoma cells, reported to have a methylated E-cadherin promoter (53). As the expression level of SIP1 in the described cell lines is in common with snail mRNA expression in E-cadherin negative cell lines (66), we looked for snail expression levels in our conditional SIP1 expressing cell line MDCK-Tetoff-SIP1. Snail expression could not be detected after SIP1 induction. E-cadherin repression is in our cell system not snail related.

SIP1 enhances the malignant phenotype by promoting loss of cell adhesion and invasion. As E-cadherin is a well-known invasion-suppressor molecule (47), we addressed the question whether SIP1 induction switches the cells to a more invasive phenotype. A cell aggregation assay was performed of non-induced versus induced MDCK-Tetoff-SIP1 cells. The non-induced MDCK-Tetoff-SIP1 cells showed significant aggregation after 30 minutes, but SIP1 induction abrogated normal cell-cell aggregation to a similar extent as an E-cadherin blocking antibody DECMA-1. Invasion into collagen type-I gels was induced by SIP1 as efficiently as by the DECMA-1 antibody.

SIP1-expression results in the reduction of unidirectional cell migration. The role of E-cadherin on cell migration was demonstrated by using a blocking E-cadherin with a specific antibody that results in a reduction of unidirectional cell migration (72). The effect of SIP1 expression on different cell migration due to down regulation of E-cadherin was studied in a wound assay in the inducible MDCK-Tetoff SIP1 expressing cell line. We could demonstrate that induction of SIP1 results in a lower unidirectional cell migration. Down regulation of E-cadherin mediated cell-cell contact results in the disturbance of unidirectional migration.

DISCUSSION: Invasion and metastasis are believed to be the most crucial steps in tumor progression. Malignancy of carcinoma cells is characterized by loss of both cell-cell adhesion and cellular differentiation and this has been frequently reported to correlate negatively with E-cadherin down-regulation. Loss of E-cadherin expression has been attributed to transcriptional dysregulation (52, 73). We show here that the zinc finger protein SIP1 represses E-cadherin expression at the transcriptional level by binding to the conserved E-boxes present in the minimal E-cadherin promoter. The specific binding of SIP1 on the two E-boxes was confirmed by mutagenesis of either the zinc finger clusters of SIP1 or the E-box sequences in the E-cadherin promoter. Indeed, such mutations resulted in the loss of repression of the E-cadherin promoter activity by SIP1. These results are compatible with the finding that comparable mutations of the E-boxes resulted in the up regulation of the E-cadherin promoter activity in E-cadherin-negative cell lines, where the wild-type promoter shows low activity (Refs. 56, 58). Stable transfection of the transcriptional repressor SIP1 induces down regulation of E-cadherin at both mRNA and protein level. A wound assay demonstrates that SIP1 interferes with the unidirectional migration mediated by a functional E-cadherin cell-cell contact. Weaker cell-cell contact results in more multi-directional migration of the epithelial cells. A striking correlation between down-regulated E-cadherin and up-regulated SIP1 expression was seen in various human tumor cells. Finally, we demonstrate here that the down regulation of E-cadherin due to SIP1 expression is also associated with a remarkable increase of the invasion capacity. Hence, SIP1 can be considered as an invasion-inducer due to its binding to the E-cadherin promoter. The fact that the transcriptional repressor Snail also specifically binds E-boxes resulting in transcriptional E-cadherin repression (66, 67) raised the question whether the E-cadherin repression in our studies is Snail-mediated. Snail mRNA up-regulation could not be detected in the conditional SIP1 expressing MDCK-Tetoff-SIP1 cell line. These data led us to consider SIP1 as the effector of transcriptional E-cadherin repression in our cell system. This idea was supported by the fact that mutations of the E-boxes have a more extensive effect on the decrease of repression of the E-cadherin promoter when cotransfected with SIP1. Derepression of the E-cadherin promoter activity, when cotransfected with SIP1, is already detected with a single E-box mutation. For Snail cotransfection a clear derepression effect was only seen when more E-boxes were mutated in the human E-cadherin promoter (66). The high expression of SIP1 in the breast cancer cell lines MDA-MB435S and MDA-MB231 is remarkable. These tumor cell lines have been described to bear a hypermethylated E-cadherin promoter (53). However, this should not rule out an important role for SIP1 repression of the endogenous E-cadherin promoter. Mutations of the E-boxes reactivate the exogenous E-cadherin promoter activity strongly in these cell lines. Indeed, recent research made clear that many transcription factors function by recruiting multiprotein complexes with chromatin modifying activities to specific sites on DNA (74). It was already shown that another Smad-interacting transcription factor TGIF associates with histone deacetylase (75). DNA methylation and chromatin condensation could therefore act synergistically with histone deacetylation to repress gene transcription (76).

Materials and methods—Cell Culture and reagents—The MDCK-Tetoff cell line was obtained from Clonetech (Palo Alto, Calif.). This cell line is derived from the Madin Darby Canine Kidney (MDCK) Type II epithelial cell line and stably expresses the Tet-off transactivator, tTA (77). MCF7/AZ cell line is a cell line derived from MCF7, a human mammary carcinoma cell line (78). The NMe cell line is an E-cadherin expressing subclone of NMuMG, an epithelial cell line from normal mouse mammary gland (47). MDA-MB231 is a human breast cancer cell line (ATCC, Manassas, Va.).

Plasmids: The full-size mouse SIP1 cDNA sequence was cloned into the Myc-tag containing pCS3 eukaryotic expressing vector derived from pCS2 (69). The resulting plasmid was designated "pCS3-SIP1FS." Remacle et al. (68) described mutagenesis of the zinc finger clusters of the SIP1. For the construction of the inducible vector pUHD10.3SIP1, a ClaI/XbaI fragment from pCS3SIP1FS was cloned into the EcoRI/XbaI-cut pUHD10.3 vector (79). The ClaI site of SIP1 fragment and the EcoRI site of the vector were blunted using Pfu polymerase (Stratagene; La Jolla, Calif.). The E-cadherin promoter sequence (−341/+41) was obtained by PCR on genomic DNA from the human MCF7/AZ cell line. PCR-primers used are: 5'-ACAAAAGAACTCAGCCAAGTG-3' (SEQ ID NO:42) and 5'-CCGCAAGCTCACAGGTGC-3' (SEQ ID NO:43). The GC-melt kit (Clonetech; Palo Alto, Calif.) was used for efficient amplification. The PCR product was blunted, kinased and then cloned into the pGL3 basic vector (Promega; Madison, Wis.), which was opened at the SrfI site. By using the KpnI-HindIII sites in this luciferase reporter construct, the E-cadherin promoter was also transferred to the pGL3 enhancer vector. Mutagenesis of the E-boxes in the human E-cadherin promoter was performed by the QUICKCHANGE™ Site-Directed Mutagenesis Kit (Stratagene) using the following primers:

```
forward primer E-box1:
5'-gctgtggccggCAGATGaaccctcag-3';      (SEQ ID NO:44)

reverse primer E-box1:
5'-ctgagggttCATCTGccggccacagc-3';      (SEQ ID NO:45)

forward primer E-box3:
5'-gctccgggctCATCTGgctgcagc-3';        (SEQ ID NO:46)

reverse primer E-box3:
5'-gctgcagcCAGATGagccccggagc-3'.       (SEQ ID NO:47)
```

Stable transfection of cells: For stable transfection of the MDCK-Tetoff cell line, the LipofectAMINE PLUS™ (Gibco BRL, Rockville, Md.) method was used. 2000 cells were grown on a 75 cm² falcon for 24 hours and then transfected with 30 μg of pUHD10.3-SIP1 plasmid plus 3 μg pPHT plasmid. The latter is a pPNT derivative and confers resistance to hygromycin (80). Stable MDCK-Tetoff transfectants, MDCK-Tetoff-SIP1, were selected by hygromycin-B (150 units/ml) (Duchefa Biochemie, Haarlem, NL) for a period of two weeks. Induction of SIP1 was prevented by adding tetracycline (1 μg/μl) (Sigma Chemicals, US). Expression of SIP1 was done by washing away tetracycline at the time of subcloning. Stable clones with reliable induction properties were identified by immunofluoresence using anti-Myc tag antibodies.

Promoter reporter assays: MCF7/AZ cells were transiently transfected by using FuGENE 6 (Roche; Basel, CH). NMe and MDA-MB231 were transfected with the LIPO-FECTAMINE (Gibco BRL; Rockville, Md.) procedure and the parental MCDK cell line was transiently transfected with LIPOFECTAMINEPLUS™ (Gibco BRL; Rockville, Md.). For transient transfection, about 200,000 cells were seeded per 10-cm² well. After incubation for 24 hours, 600 ng of each plasmid type DNA was transfected. The medium was refreshed 24 hours after transfection. Cells were lysed after three days in GALACTO-STAR™ kit lysis solution (Tropix, Bedford, Mass.). Normalization of transfection was done by measuring β-galactosidase, encoded by the cotransfected pUT651 plasmid (Eurogentec; Seraing, BE). Luciferase substrate is added to each sample. For β-galactosidase detection, a chemiluminescent substrate is supplied (Tropix, Bedford, Mass.). Luciferase and β-galactosidase activity was assayed in a TOPCOUNT™ microplate scintillation reader (Packard Instrument Co., Meriden, Conn.).

Northern analysis: Total RNA was isolated with the RNeasy kit (Qiagen; Chatsworth, Calif.) following the manufacturer's protocol. Total RNA (25 μg) was glyoxylated, size-fractionated on a 1% agarose gel and transferred onto a HYBOND™-N⁺ membrane (Amersham Pharmacia Biotech, Rainhalm, UK). Hybridizations were performed as described before (81). The mouse SIP1 probe (459 bp) was generated by an EcoR-I digest of the mouse SIP1 cDNA. The human SIP1 probe (707 bp) was created by a Bst EII-NotI digest on the Kiaa 0569 clone (Kazusa DNA Research Institute). The mouse E-cadherin probe used was a SacI fragment (500 bp) of the mouse E-cadherin cDNA. Two degenerated primers: 5' CTTCCAGCAGCCCTACGAYCARGCNCA 3' (SEQ ID NO:48) and 5' GGGTGTGGGACCGGATRTGCATYTT-NAT 3' (SEQ ID NO:49) were used to amplify a fragment of the dog Snail cDNA from a total cDNA population of the MDCK cell line. Cloning and sequencing of the amplified band revealed a 432 bp cDNA fragment. To control the amount of loaded RNA, a GAPDH probe was used on the same blot. We performed the quantification of the radioactive bands on a PHOSPHOR IMAGER™ 425 (BioRad, Richmond, Calif.).

Immunofluorescence assays and Antibodies: Cells of interest were grown on glass coverslips. Fixation was by standard procedures (82). The following antibodies were used: the rat monoclonal antibody DECMA-1 (Sigma; Irvine, UK) recognizing both mouse and dog E-cadherin, and the mouse anti-Myc tag antibody (Oncogene, Cambridge, Mass.). Secondary antibodies used were Alexa 488-coupled anti-rat Ig and Alexa 594-coupled anti-mouse Ig.

Cell Aggregation Assay: Single-cell suspensions were prepared in accordance with an E-cadherin-saving procedure (83). Cells were incubated in an isotonic buffer containing 1.25 mM $Ca^{2+}$ under gyrotory shaking (New Brunswick Scientific, New Brunswick, N.J.) at 80 rpm for 30 minutes. Particle diameters were measured in a Coulter particle size counter LS200 (Coulter, Lake Placid, N.Y.) at the start ($N_o$) and after 30 minutes of incubation ($N_{30}$) and plotted against percentage volume distribution.

Collagen Invasion Assay: Six-well plates were filled with 1.25 ml of neutralized type I collagen (Upstate Biotechnology, Lake Placid, N.Y.) per well. Incubation for at least one hour at 37° C. was needed for gelification. Single-cell suspensions were seeded on top of the collagen gel and cultures were incubated at 37° C. for 24 hours. Using an inverted microscope controlled by a computer program, we counted the invasive and superficial cells in twelve fields of 0.157 mm². The invasion index expresses the percentage of cells invading the gel over the total numbers of cells (84).

Wound Assay: The wound assay was performed as described before (85). Briefly, wounded monolayers were cultured for 24 hours in serum-deprived medium in the presence or absence of tetracycline. We assessed cell migration by measuring the distance of the wound. Migration results are expressed as the average of the wound-distance.

REFERENCES

1. Arora K., H. Dai, S. G. Kazuko, J. Jamal, O. C. MB, A. Letsou and R. Warrior (1995) The *Drosophila* schnurri gene acts in the Dpp/TGF beta signaling pathway and encodes a transcription factor homologous to the human MBP family. *Cell* 81:781-90.
2. Bussemakers M. J., L. A. Giroldi, A. van Bokhoven and J. A. Schalken (1994) Transcriptional regulation of the human E-cadherin gene in human prostate cancer cell lines: characterization of the human E-cadherin gene promoter. *Biochem Biophys. Res. Commun.* 203:1284-90.
3. Fan C. M. and T. Maniatis (1990) A DNA-binding protein containing two widely separated zinc finger motifs that recognize the same DNA sequence. *Genes Dev.* 4:29-42.
4. Fortini M. E., Z. C. Lai and G. M. Rubin (1991) The *Drosophila* zfh-1 and zfh-2 genes encode novel proteins containing both zinc-finger and homeodomain motifs. *Mech. Dev.* 34:113-22.
5. Funahashi J., R. Sekido, M. Murai, Y. Kamachi and H. Kondoh (1993) Delta-crystallin enhancer binding protein delta EF1 is a zinc finger-homeodomain protein implicated in postgastrulation embryogenesis. *Development* 119:433-46.
6. Grieder N. C., D. Nellen, R. Burke, K. Basler and M. Affolter (1995) Schnurri is required for *Drosophila* Dpp signaling and encodes a zinc finger protein similar to the mammalian transcription factor PRDII-BF1. *Cell* 81:791-800.

7. Henderson L. E., T. D. Copeland, R. C. Sowder, G. W. Smythers and S. Oroszlan (1981) Primary structure of the low molecular weight nucleic acid-binding proteins of murine leukemia viruses. *J. Biol. Chem.* 256:8400-6.

8. Hendrickson W. and R. Schleif (1985) A dimer of AraC protein contacts three adjacent major groove regions of the aral DNA site. *Proc. Natl. Acad. Sci. U.S.A.* 82:3129-33.

9. Holmberg S. and P. Schjerling (1996) Cha4p of *Saccharomyces cerevisiae* activates transcription via serine/threonine response elements. *Genetics* 144:467-78.

10. Ikeda K. and K. Kawakami (1995) DNA binding through distinct domains of zinc-finger-homeodomain protein AREB6 has different effects on gene transcription. *Eur. J. Biochem.* 233:73-82.

11. Jiang Y., V. C. Yu, F. Buchholz, O. C. S, S. J. Rhodes, C. Candeloro, Y. R. Xia, A. J. Lusis, and M. G. Rosenfeld (1996) A novel family of Cys-Cys, His-Cys zinc finger transcription factors expressed in developing nervous system and pituitary gland. *J. Biol. Chem.* 271:10723-30.

12. Kim J. G. and L. D. Hudson (1992) Novel member of the zinc finger superfamily: A C2-HC finger that recognizes a glia-specific gene. *Mol. Cell. Biol.* 12:5632-9.

13. Kretzschmar M. and J. Massague (1998) SMADs: mediators and regulators of TGF-beta signaling. *Curr. Opin. Genet. Dev.* 8:103-11.

14. Kuhnlein R. P., G. Frommer, M. Friedrich, M. Gonzalez-Gaitan, A. Weber, J. F. Wagner-Bernholz, W. J. Gehring, H. Jackle and R. Schuh (1994) spalt encodes an evolutionarily conserved zinc finger protein of novel structure which provides homeotic gene function in the head and tail region of the *Drosophila* embryo. *Embo. J.* 13:168-79.

15. Kurokawa M., K. Mitani, K. Irie, T. Matsuyama, T. Takahashi, S. Chiba, Y. Yazaki, K. Matsumoto and H. Hirai (1998) The oncoprotein Evi-1 represses TGF-beta signaling by inhibiting Smad3. *Nature* 394:92-6.

16. Latinkic B. V., M. Umbhauer, K. A. Neal, W. Lerchner, J. C. Smith and V. Cunliffe (1997) The *Xenopus* Brachyury promoter is activated by FGF and low concentrations of activin and suppressed by high concentrations of activin and by paired-type homeodomain proteins [published erratum appears in *Genes Dev.* 1998 Apr. 15;12(8): 1240]. *Genes Dev.* 11:3265-76.

17. Lerchner W., J. E. Remacle, D. Huylebroeck and J. C. Smith. Unpublished observations.

18. Maxam A. M. and W. Gilbert (1980) Sequencing end-labeled DNA with base-specific chemical cleavages. Methods Enzymol. 65:499-560.

19. Miller J., A. D. McLachlan and A. Klug (1985) Repetitive zinc-binding domains in the protein transcription factor 111A from *Xenopus* oocytes. *Embo. J.* 4:1609-14.

20. Morishita K., K. Suzukawa, T. Taki, J. N. Ihle and J. Yokota (1995) EVI-1 zinc finger protein works as a transcriptional activator via binding to a consensus sequence of GACAAGATAAGATAAN1-28 CTCATCTTC. *Oncogene* 10:1961-7.

21. Mount S. M. and G. M. Rubin (1985) Complete nucleotide sequence of the *Drosophila* transposable element copia: homology between copia and retroviral proteins. *Mol. Cell Biol.* 5:1630-8.

22. Nucifora G. (1997) The EVIL gene in myeloid leukemia. *Leukemia* 11:2022-31.

23. Postigo A. A. and D. C. Dean (1997) ZEB, a vertebrate homolog of *Drosophila* Zfh-1, is a negative regulator of muscle differentiation. *Embo. J.* 16:3935-43.

24. Rajavashisth T. B., A. K. Taylor, A. Andalibi, K. L. Svenson and A. J. Lusis (1989) Identification of a zinc finger protein that binds to the sterol regulatory element. *Science* 245:640-3.

25. Ray D., R. Bosselut, J. Ghysdael, M. G. Mattei, A. Tavitian and F. Moreau-Gachelin (1992) Characterization of Spi-B, a transcription factor related to the putative oncoprotein Spi-1/PU.1. *Mol. Cell Biol.* 12:4297-304.

26. Rosen G. D., J. L. Barks, M. F. Iademarco, R. J. Fisher and D. C. Dean (1994) An intricate arrangement of binding sites for the Ets family of transcription factors regulates activity of the alpha 4 integrin gene promoter. *J. Biol. Chem.* 269:15652-60.

27. Rupp R. A., L. Snider and H. Weintraub (1994) *Xenopus* embryos regulate the nuclear localization of XMyoD. *Genes Dev.* 8:1311-23.

28. Schwabe J. W. and D. Rhodes (1991) Beyond zinc fingers: steroid hormone receptors have a novel structural motif for DNA recognition. *Trends Biochem. Sci.* 16:291-6.

29. Seeler J. S., C. Muchardt, A. Suessle and R. B. Gaynor (1994) Transcription factor PRDII-BF1 activates human immunodeficiency virus type 1 gene expression. *J. Virol.* 68:1002-9.

30. Sekido R., K. Murai, J. Funahashi, Y. Kamachi, A. Fujisawa-Sehara, Y. Nabeshima and H. Kondoh (1994) The delta-crystallin enhancer-binding protein delta EF1 is a repressor of E2-box-mediated gene activation. *Mol. Cell Biol.* 14:5692-700.

31. Sekido R., K. Murai, Y. Kamachi and H. Kondoh (1997) Two mechanisms in the action of repressor deltaEF1: binding site competition with an activator and active repression. *Genes Cells* 2:771-83.

32. Todd R. B. and A. Andrianopoulos (1997) Evolution of a fungal regulatory gene family: the Zn(II)2Cys6 binuclear cluster DNA binding motif. *Fungal Genet. Biol.* 21:388-405.

33. van't Veer L. J., P. M. Lutz, K. J. Isselbacher and R. Bernards (1992) Structure and expression of major histocompatibility complex-binding protein 2, a 275-kDa zinc finger protein that binds to an enhancer of major histocompatibility complex class I genes. *Proc. Natl. Acad. Sci. U.S.A.* 89:8971-5.

34. Verschueren K., J. E. Remacle, C. Collart, H. Kraft, B. S. Baker, P. Tylzanowski, L. Nelles, G. Wuytens, M. T. Su, R. Bodmer, J. Smith and D. Huylebroeck (1999) SIP1, a novel zinc finger/homeodomain repressor, interacts with Smad proteins and binds to 5'-CACCT sequences in candidate target genes. *J. Biol. Chem.*

35. Watanabe Y., K. Kawakami, Y. Hirayama and K. Nagano (1993) Transcription factors positively and negatively regulating the Na,K-ATPase alpha 1 subunit gene. *J. Biochem.* (Tokyo) 114:849-55.

36. Yee K. S. and V. C. Yu (1998) Isolation and characterization of a novel member of the neural zinc finger factor/myelin transcription factor family with transcriptional repression activity. *J. Biol. Chem.* 273:5366-74.

37. Brent R. and M. Ptashne (1985) A eukaryotic transcriptional activator bearing the DNA specificity of a prokaryotic repressor. *Cell* 43:729-736.

38. Chien C. T., P. L. Bartel, R. Stemglanz and S. Fields (1991) The two-hybrid system: a method to identify and clone genes for proteins that interact with a protein of interest. *Proc. Natl. Acad. Sci. U.S.A.* 88:9578-9582.

39. Durfee T., K. Becherer, P. L. Chen, S. H. Yeh, Y. Yang, A. E. Kilburn, W. H. Lee and S. J. Elledge (1993) The retinoblastoma protein associates with the protein phosphatase type 1 catalytic subunit. *Genes Dev.* 7:555-569.

40. Gyuris J., E. Golemis, H. Chertkov and R. Brent (1993) Cdi1, a human G1 and S phase protein phosphatase that associates with Cdk2. *Cell* 75:791-803.

41. Silver P. A., R. Brent and M. Ptashne (1986) DNA binding is not sufficient for nuclear localisation of regulatory proteins in *Saccharomyces cerevisiae*. *Mol. Cell Biol.* 6:4763-4766.

42. Yocum R. R., S. Hanley, R. J. West and M. Ptashne (1984) Use of lacZ fusions to delimit regulatory elements of the inducible divergent GAL1-GAL10 promoter in *Saccharomyces cerevisiae*. *Mol. Cell Biol.* 4:1985-1998.

43. de Groot R. P. and W. Kruijer (1990) Transcriptional activation by TGF beta 1 mediated by the dyad symmetry element (DSE) and the TPA responsive element (TRE). *Biochem. Biophys. Res. Commun.* 168:1074-1081.

44. Kroll K. L. and L. Amaya (1996) Transgenic *Xenopus* embryos from sperm nuclear transplantations reveal FGF signaling requirements during gastrulation. *Development* 122:3173-3183.

45. Niewkoop P. D. and J. Faber (1967) Normal Table of *Xenopus laevis* (Daudin). Amsterdam, North Holland.

46. Frixen U. H. et al. (1991) E-cadherin-mediated cell-cell adhesion prevents invasiveness of human carcinoma cells. *Journal of Cell Biology* 113:173-185.

47. Vleminckx K., L. Vakaet Jr, M. Mareel, W. Fiers and F. van Roy (1991) Genetic manipulation of E-cadherin expression by epithelial tumour cells reveals an invasion suppressor role. *Cell* 66:107-119.

48. Perl A. K., P. Wilgenbus, U. Dahl, H. Semb and G. Christofori (1998) A causal role for E-cadherin in the transition from adenoma to carcinoma. *Nature* (London) 392: 190-193.

49. Potter E., C. Bergwitz and G. Brabant (1994) The cadherin-catenin system: Implications for growth and differentiation of endocrine tissues. *Endocrine Reviews* 20:207-239.

50. Becker K. F. et al. (1994) E-cadherin gene mutations provide clues to diffuse type gastric carcinomas. *Cancer Research* 54:3845-3852.

51. Berx G., F. Nollet and F. van Roy (1998) Dysregulation of the E-cadherin/catenin complex by irreversible mutations in human carcinomas. *Cell Adhesion and Communication* 6:171-184.

52. Brabant G. et al. (1993) E-cadherin—a differentiation marker in thyroid malignancies. *Cancer Research* 53:4987-4993.

53. Graff J. R. et al. (1995) E-cadherin expression is silenced by DNA hypermethylation in human breast and prostate carcinomas. *Cancer Research* 55:5195-5199.

54. Yoshiura K. et al. (1995) Silencing of the E-cadherin invasion-suppressor gene by CpG methylation in human carcinomas. *Proc. Natl. Acad. Sci. U.S.A.* 92:7416-7419.

55. Behrens J., O. Lowrick, L. Klein-Hitpass and W. Birchmeier (1991) The E-cadherin promoter: functional analysis of a G°C-rich region and an epithelial cell-specific palindromic regulatory element. *Proc. Natl. Acad. Sci. U.S.A.* 88:11495-11499.

56. Giroldi L. A. et al. (1997) Role of E boxes in the repression of E-cadherin expression. *Biochemical and Biophysical Research Communications* 241:453-458.

57. Hennig G. et al. (1995) Progression of carcinoma cells is associated with alterations in chromatin structure and factor binding at the E-cadherin promoter in vivo. Oncogene 11, 475-484.

58. Ji X. D., A. S. Woodard, D. L. Rimm and E. R. Fearon (1997) Transcriptional defects underlie loss of E-cadherin expression in breast cancer. *Cell Growth & Differentiation* 8:773-778.

59. Hajra K. M., X. D. Ji and E. R. Fearon (1999) Extinction of E-cadherin expression in breast cancer via a dominant repression pathway acting on proximal promoter elements. *Oncogene* 18:7274-7279.

60. Miettinen P. J., R. Ebner, A. R. Lopez and R. Derynck (1994) TGF-beta induced transdifferentiation of mammary epithelial cells to mesenchymal cells: involvement of type I receptors. *Journal of Cell Biology* 127:2021-2036.

61. Shiozaki H. et al. (1995) Effect of epidermal growth factor on cadherin-mediated adhesion in a human oesophageal cancer cell line. *British Journal of Cancer* 71:250-258.

62. Reichmann E. et al. (1992) Activation of an inducible c-FosER fusion protein causes loss of epithelial polarity and triggers epithelial-fibroblastoid cell conversion. *Cell* 71:1103-1116.

63. Batsche E., C. Muchardt, J. Behrens, H. C. Hurst and C. Cremisi (1998) RB and c-Myc activate expression of the E-cadherin gene in epithelial cells through interaction with transcription factor AP-2. *Molecular and Cellular Biology* 18: 1-12.

64. Torban E. and P. R. Goodyer (1998) Effects of PAX2 expression in a human fetal kidney (HEK293) cell line. *Biochimica et Biophysica Acta—Molecular Cell Research* 1401:53-62.

65. Spath G. F. and M. C. Weiss (1998) Hepatocyte nuclear factor 4 provokes expression of epithelial marker genes, acting as a morphogen in dedifferentiated hepatoma cells. *Journal of Cell Biology* 140:935-946.

66. Batlle E. et al. (2000) The transcription factor Snail is a repressor of E-cadherin gene expression in epithelial tumour cells. *Nature Cell Biology* 2:84-89.

67. Cano A. et al. (2000) The transcription factor Snail controls epithelial-mesenchymal transitions by repressing E-cadherin expression. *Nature Cell Biology* 2:76-83.

68. Remacle J. E. et al. (1999) New mode of DNA binding of multi-zinc finger transcription factors: deltaEF1 family members bind with two hands to two target sites. *EMBO Journal* 18:5073-5084.

69. Verschueren K. et al. (1999) SIP1, a novel zinc finger/homeodomain repressor, interacts with Smad proteins and binds to 5'-CACCT sequences in candidate target genes. *Journal of Biological Chemistry* 274:20489-20498.

70. Derynck R., Y. Zhang X. H. Feng (1998) Smads: transcriptional activators of TGFbeta-responses. *Cell* 95:737-740.

71. Massague J. (1998) TGF-beta signal transduction. *Annual Review of Biochemistry* 67:753-791.

72. Andre F. et al. (1999) Integrins and E-cadherin cooperate with IGF-I to induce migration of epithelial colonic cells. *International Journal of Cancer* 83:497-505.

73. Hirohashi S. (1998) Inactivation of the E-cadherin-mediated cell adhesion system in human cancers. *American Journal of Pathology* 153:333-339.

74. Bird A. P. and A. P. Wolffe (1999) Methylation-induced repression—Belts, braces, and chromatin. *Cell* 99:451-454.

75. Wotton D., R. S. Lo, S. Lee and J. Massague (1999) A Smad transcriptional corepressor. *Cell* 97:29-39.

76. Cameron E. E., K. E. Bachman, S. Myohanen, J. G. Herman and S. B. Baylin (1999) Synergy of demethylation and histone deacetylase inhibition in the re-expression of genes silenced in cancer. *Nature Genetics* 21:103-107.

77. Gossen M. et al. (1995) Transcriptional activation by tetracyclines in mammalian cells. *Science* (Washington D.C.) 268:1766-1769.
78. Bracke M. E., N. A. Van Larebeke, B. M. Vyncke and M. M. Mareel (1991) Retinoic acid modulates both invasion and plasma membrane ruffling of MCF-7 human mammary carcinoma cells in vitro. *British Journal of Cancer* 63:867-872.
79. Gossen M. and H. Bujard (1992) Tight control of gene expression in mammalian cells by tetracycline-responsive promoters. *Proc. Natl. Acad. Sci. U.S.A.* 89:5547-5551.
80. Tybulewicz V. L. J., C. E. Crawford, P. K. Jackson, R. T. Bronson and R. C. Mulligan (1991) Neonatal lethality and lymphopenia in mice with a homozygous disruption of the c-abl proto-oncogene. *Cell* 65:1153-1163.
81. Bussemakers M. J. G., W. J. M. Van de Ven, F. M. J. Debruyne and J. A. Schalken (1991) Identification of High Mobility Group Protein I(Y) as potential progression marker for prostate cancer by differential hybridization analysis. *Cancer Research* 51:606-611.
82. J. van Hengel, P. Vanhoenacker, K. Staes and F. van Roy (1999) Nuclear localization of the p120$^{ctn}$ Armadillo-like catenin is counteracted by a nuclear export signal and by E-cadherin expression. *Proc. Natl. Acad. Sci. U.S.A.* 96:7980-7985.
83. Bracke M. E. et al. (1993) Insulin-like growth factor I activates the invasion suppressor function of E-cadherin in MCF-7 human mammary carcinoma cells in vitro. *British Journal of Cancer* 68:282-289.
84. Bracke M. E., T. Boterberg, E. A. Bruyneel and M. M. Mareel (1999) in *Metastasis Methods and Protocols* (eds. S. Brooks and U. Schumacher) In press (Humana Press, Totowa).
85. Andre F. et al. (1999) Protein kinase C-gamma and -delta are involved in insulin-like growth factor I-induced migration of colonic epithelial cells. *Gastroenterology* 116:64-77.

What is claimed is:

1. A test kit, said test kit comprising:
an isolated nucleotide sequence comprising CACCT-N-AGGTG (SEQ ID NO:1 and SEQ ID NO:3 separated by N), wherein N is a spacer of a length selected from the group consisting of 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44; and
a protein capable of binding said nucleotide sequence.

2. A test kit, said test kit comprising:
an isolated nucleic acid sequence comprising CACCT-N-AGGTG (SEQ ID NO:1 and SEQ ID NO:3 separated by N), wherein N is a spacer of a length selected from the group consisting of 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

3. An isolated nucleic acid sequence comprising CACCT-N-AGGTG (SEQ ID NO:1 and SEQ ID NO:3 separated by N wherein N is a spacer of a length consisting of 1, 2, 3, 4, 5, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

4. A test kit, said test kit comprising:
an isolated nucleotide sequence comprising CACCT-N-CACCT (a first SEQ ID NO:1 and a second SEQ ID NO:1 separated by N), wherein N is a spacer of a length selected from the group consisting of 1, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44; and
a protein capable of binding said nucleotide sequence.

5. A test kit, said test kit comprising:
an isolated nucleotide sequence comprising CACCT-N-CACCT (a first SEQ ID NO:1 and a second SEQ ID NO:1 separated by N), wherein N is a spacer of a length selected from the group consisting of 1, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

6. An isolated nucleic acid sequence comprising CACCT-N-CACCT (a first SEQ ID NO:1 and a second SEQ ID NO:1 separated by N), wherein N is a spacer of a length selected from the group consisting of 1, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

7. A test kit, said test kit comprising:
an isolated nucleotide sequence comprising CACCT-N-CACCT (a first SEQ ID NO:1 and a second SEQ ID NO:1 separated by N), wherein N is a spacer sequence greater than 0 base pairs and 44 or less base pairs in length; and
a protein having separated clusters of zinc fingers and capable of binding said nucleotide sequence.

8. A test kit, said test kit comprising:
an isolated nucleotide sequence comprising CACCT-N-AGGTG (SEQ ID NO:1 and SEQ ID NO:3 separated by N), wherein N is a spacer sequence greater than 0 base pairs and 44 or less base pairs in length; and
a protein having separated clusters of zinc fingers and capable of binding said nucleotide sequence.

9. A test kit, said test kit comprising:
an isolated nucleotide sequence comprising AGGTG-N-AGGTG (a first SEQ ID NO:3 and a second SEQ ID NO:3 separated by N), wherein N is a spacer of a length selected from the group consisting of 1, 2, 3, 4, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44; and
a protein capable of binding said nucleotide sequence.

10. A test kit, said test kit comprising:
an isolated nucleotide sequence comprising AGGTG-N-AGGTG (a first SEQ ID NO:3 and a second SEQ ID NO:3 separated by N), wherein N is a spacer sequence greater than 0 base pairs and 44 or less base pairs in length; and
a protein having separated clusters of zinc fingers and capable of binding said nucleotide sequence.

11. A test kit, said test kit comprising:
an isolated nucleotide sequence comprising AGGTG-N-AGGTG (a first SEQ ID NO:3 and a second SEQ ID NO:3 separated by N), wherein N is a spacer of a length selected from the group consisting of 1, 2, 3, 4, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

12. An isolated nucleic acid sequence comprising AGGTG-N-AGGTG (a first SEQ ID NO:3 and a second SEQ ID NO:3 separated by N), wherein N is a spacer of a length selected from the group consisting of 1, 2, 3, 4, 6, 7, 8, 9, 10, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

13. A test kit, said test kit comprising:
an isolated nucleotide sequence comprising AGGTG-N-CACCT (SEQ ID NO:3 and SEQ ID NO:1 separated by N), wherein N is a spacer of a length selected from the group consisting of 1, 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44; and
a protein capable of binding said nucleotide sequence.

14. A test kit, said test kit comprising:
an isolated nucleotide sequence comprising AGGTG-N-CACCT (SEQ ID NO:3 and SEQ ID NO:1 separated by N), wherein N is a spacer sequence greater than 0 base pairs and 44 or less base pairs in length; and
a protein having separated clusters of zinc fingers and capable of binding said nucleotide sequence.

15. A test kit, said test kit comprising:
an isolated nucleotide sequence comprising AGGTG-N-CACCT (SEQ ID NO:3 and SEQ ID NO:1 separated by N), wherein N is a spacer of a length selected from the group consisting of 1, 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

16. An isolated nucleic acid sequence comprising AGGTG-N-CACCT (SEQ ID NO:3 and SEQ ID NO:1 separated by N), wherein N is a spacer of a length selected from the group consisting of 1, 2, 3, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 41, 42, 43, and 44.

* * * * *

UNITED STATES PATENT AND TRADEMARK OFFICE
CERTIFICATE OF CORRECTION

| | | |
|---|---|---|
| PATENT NO. | : 7,435,806 B2 | Page 1 of 2 |
| APPLICATION NO. | : 11/196670 | |
| DATED | : October 14, 2008 | |
| INVENTOR(S) | : Danny Huylebroeck, Kristin Verschueren and Jacques Remacle | |

It is certified that error appears in the above-identified patent and that said Letters Patent is hereby corrected as shown below:

Original as-filed paragraphs [0011], [0012], and [0013] were incorrectly deleted by the Patent Office during prosecution when the amendment submitted by applicants on September 28, 2007, replacing paragraphs [00111], [00112], and [00113] was entered. Therefore, the following corrections need to be made:

COLUMN 3, LINE 48, through and including COLUMN 4, LINE 38, delete "Stable transfection of cells: For . . ." through and including "Rad, Richmond Calif.)."

COLUMN 3, LINE 48, through and including COLUMN 4, LINE 38, re-insert the following original paragraphs:
--This binding may be generalized to other transcription factors that contain separated clusters of zinc fingers and may be applied to other Smad-binding proteins. Moreover, the Smad-interacting protein SIP1 shows high expression in E-cadherin-negative human carcinoma cell lines, resulting in down regulation of E-cadherin transcription. Conditional expression of SIP1 in E-cadherin-positive MDCK cells also abrogates E-cadherin-mediated intercellular adhesion and simultaneously induced invasion. Hence, SIP1 can considered as a potent invasion promoter molecule and compounds, such as anti-SIP1 antibodies, small molecules specifically binding to SIP, anti-sense nucleic acids and ribozymes, which interfere with SIP1 production or activity can prevent tumor invasion and metastasis.--

Signed and Sealed this
Seventh Day of June, 2011

David J. Kappos
*Director of the United States Patent and Trademark Office*

CERTIFICATE OF CORRECTION (continued)
U.S. Pat. No. 7,435,806 B2

--The invention thus includes a method of identifying transcription factors such as activators and/or repressors. The method comprises providing cells with a nucleic acid sequence at least comprising a sequence CACCT (SEQ ID NO:1) or AGGTG (SEQ ID NO:3) (preferably, twice the CACCT (SEQ ID NO:1) sequence) as bait for the screening of a library encoding potential transcription factors and performing a specificity test to isolate the factors.--

--In another embodiment, the bait comprises one of the sequences CACCT-N-CACCT (a first SEQ ID NO:1 and a second SEQ ID NO:1 separated by N), CACCT-N-AGGTG (SEQ ID NO:1 and SEQ ID NO:3 separated by N), AGGTG-N-CACCT (SEQ ID NO:3 and SEQ ID NO:1 separated by N) or AGGTG-N-AGGTG (a first SEQ ID NO:3 and a second SEQ ID NO:3 separated by N) wherein N is a spacer sequence. The latter spacer sequence can vary in length and can contain any number of base pairs ("bp") from N=0 bp to N= at least 44 bp. Thus, for example, N can be 0, 1, 2, 3, 4, 5, 6, 7, 8, 9, 10, 15, 20, 25, 30, 35, 40, 45, 50, 60, 70, 80, 90, 100, 200, 300 or 400 bp in length.--

| | | |
|---|---|---|
| COLUMN 31, | LINE 14, | change "LipofectAMINE PLUS™" to to --LIPOFECTAMINEPLUS™ (transfection reagent)-- |
| COLUMN 31, | LINE 29, | change "FuGENE 6" to --FUGENE® 6 (transfection reagent)-- |
| COLUMN 31, | LINES 30, 31, | change "LIPOFECTAMINE" to --LIPOFECTAMINE™ (transfection reagent)-- |
| COLUMN 31, | LINE 34, | change "LIPOFECTAMINEPLUS™" to --LIPOFECTAMINEPLUS™ (transfection reagent)-- |
| COLUMN 31, | LINE 39, | change "GALACTO-STAR™" to --GALACTON-STAR® (chemiluminescence reagent)-- |
| COLUMN 31, | LINE 46, | change "TOPCOUNT™" to --TOPCOUNT®-- |
| COLUMN 31, | LINE 53, | change "HYBOND™-N$^+$" to --HYBOND®-N$^+$-- |
| COLUMN 32, | LINE 2, | change "PHOSPHOR IMAGER™ 425" to --PHOSPHORIMAGER® (image reader) 425-- |

```
                        SEQUENCE LISTING

<160> NUMBER OF SEQ ID NOS: 66

<210> SEQ ID NO 1
<211> LENGTH: 5
<212> TYPE: DNA
<213> ORGANISM: Artificial
<220> FEATURE:
<221> NAME/KEY: misc_feature
<223> OTHER INFORMATION: Description of Artificial Sequence: Portion of
      bait for screening

<400> SEQUENCE: 1 cacct                                                                    5

<210> SEQ ID NO 2
<211> LENGTH: 6
<212> TYPE: DNA
<213> ORGANISM: Artificial
<220> FEATURE:
<221> NAME/KEY: misc_feature
<223> OTHER INFORMATION: Description of Artificial Sequence: portion of
      bait for screening

<400> SEQUENCE: 2 cacctg                                                                   6

<210> SEQ ID NO 3
<211> LENGTH: 5
<212> TYPE: DNA
<213> ORGANISM: Artificial
<220> FEATURE:
<221> NAME/KEY: misc_feature
<223> OTHER INFORMATION: Description of Artificial Sequence: portion of
      bait for screening

<400> SEQUENCE: 3 aggtg                                                                    5

<210> SEQ ID NO 4
<211> LENGTH: 7
<212> TYPE: DNA
<213> ORGANISM: Artificial
<220> FEATURE:
<221> NAME/KEY: misc_feature
<223> OTHER INFORMATION: Description of Artificial Sequence: consensus
``` element for binding of MyT1, NZF 1 and NZF 3

<400> SEQUENCE: 4 aaagttt                                                                7

<210> SEQ ID NO 5
<211> LENGTH: 52
<212> TYPE: DNA
<213> ORGANISM: Artificial
<220> FEATURE:
<221> NAME/KEY: misc_feature
<223> OTHER INFORMATION: Description of Artificial Sequence: complex
      consensus sequence
<220> FEATURE:
<221> NAME/KEY: misc_feature
<222> LOCATION: (16)..(43)
<223> OTHER INFORMATION: nucleotides 16 43 represent a spacer sequence
      wherein any one, more, or all of nucleotides 16 43 my be present
      or absent

<400> SEQUENCE: 5
gacaagataa gataannnnn nnnnnnnnnn nnnnnnnnnn nnnctcatct tc              52

<210> SEQ ID NO 6
<211> LENGTH: 30
<212> TYPE: DNA
<213> ORGANISM: Artificial
<220> FEATURE:
<221> NAME/KEY: misc_feature
<223> OTHER INFORMATION: Description of Artificial Sequence: primer SIP1
      NZF3Mut

<400> SEQUENCE: 6
ccacctgaaa gaatccctga gaattcacag                                       30

<210> SEQ ID NO 7
<211> LENGTH: 30
<212> TYPE: DNA
<213> ORGANISM: Artificial
<220> FEATURE:
<221> NAME/KEY: misc_feature
<223> OTHER INFORMATION: Description of Artificial Sequence: primer SIP1
      CZF2Mut

<400> SEQUENCE: 7
gggtcctaca gttcatctat cagcagcaag                                       30

<210> SEQ ID NO 8
<211> LENGTH: 30
<212> TYPE: DNA
<213> ORGANISM: Artificial
<220> FEATURE:
<221> NAME/KEY: misc_feature
<223> OTHER INFORMATION: Description of Artificial Sequence: primer SIP1
      NZF4Mut

<400> SEQUENCE: 8
caccacctta tcgagtcctc gaggctgcac                                       30

<210> SEQ ID NO 9
<211> LENGTH: 30
<212> TYPE: DNA
<213> ORGANISM: Artificial
<220> FEATURE:
<221> NAME/KEY: misc_feature
<223> OTHER INFORMATION: Description of Artificial Sequence: primer SIP1
      CZF3Mut

<400> SEQUENCE: 9

```
tcctactcgc agtccatgaa tcacaggtac                                       30

<210> SEQ ID NO 10
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      WT

<400> SEQUENCE: 10
atccaggcca cctaaaatat agaatgataa agtgaccagg tgtcagttct                 50

<210> SEQ ID NO 11
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      D

<400> SEQUENCE: 11
atccaggcca cctaaaatat agaatgataa agtgaccaga tgtcagttct                 50

<210> SEQ ID NO 12
<211> LENGTH: 23
<212> TYPE: DNA
<213> ORGANISM: Artificial
<220> FEATURE:
<221> NAME/KEY: misc_feature
<223> OTHER INFORMATION: Description of Artificial Sequence: probe Xbra
      E

<400> SEQUENCE: 12
taaagtgacc aggtgtcagt tct                                              23

<210> SEQ ID NO 13
<211> LENGTH: 27
<212> TYPE: DNA
<213> ORGANISM: Artificial
<220> FEATURE:
<221> NAME/KEY: misc_feature
<223> OTHER INFORMATION: Description of Artificial Sequence: probe Xbra
      F

<400> SEQUENCE: 13
atccaggcca cctaaaatat agaatga                                          27

<210> SEQ ID NO 14
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Rdm +
      Xbra E

<400> SEQUENCE: 14
caatttagag tactgtgtac ttgggagtaa agtgaccagg tgtcagttct                 50

<210> SEQ ID NO 15
<211> LENGTH: 53
<212> TYPE: DNA
<213> ORGANISM: Artificial
<220> FEATURE:
```

```
<221> NAME/KEY: misc_feature
<223> OTHER INFORMATION: Description of Artificial Sequence: probe Xbra
      F + AREB6

<400> SEQUENCE: 15
atccaggcca cctaaaatat agaatgaggc tcagacaggt gtagaattcg gcg           53

<210> SEQ ID NO 16
<211> LENGTH: 53
<212> TYPE: DNA
<213> ORGANISM: Artificial
<220> FEATURE:
<221> NAME/KEY: misc_feature
<223> OTHER INFORMATION: Description of Artificial Sequence: probe Rdm +
      AREB6

<400> SEQUENCE: 16
caatttagag tactgtgtac ttgggagggc tcagacaggt gtagaattcg gcg           53

<210> SEQ ID NO 17
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      J

<400> SEQUENCE: 17
gcacaggcca cctaaaatat agaatgataa agtgaccagg tgtcagttct                50

<210> SEQ ID NO 18
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      K

<400> SEQUENCE: 18
atcactgcca cctaaaatat agaatgataa agtgaccagg tgtcagttct                50

<210> SEQ ID NO 19
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      L

<400> SEQUENCE: 19
atccagtaaa cctaaaatat agaatgataa agtgaccagg tgtcagttct                50

<210> SEQ ID NO 20
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      M

<400> SEQUENCE: 20
atccaggccc aataaaatat agaatgataa agtgaccagg tgtcagttct                50
```

```
<210> SEQ ID NO 21
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      N

<400> SEQUENCE: 21
atccaggcca ccgccaatat agaatgataa agtgaccagg tgtcagttct            50

<210> SEQ ID NO 22
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      O

<400> SEQUENCE: 22
atccaggcca cctaaccgat agaatgataa agtgaccagg tgtcagttct            50

<210> SEQ ID NO 23
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      P

<400> SEQUENCE: 23
atccaggcca cctaaaatcg cgaatgataa agtgaccagg tgtcagttct            50

<210> SEQ ID NO 24
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      Q

<400> SEQUENCE: 24
atccaggcca cctaaaatat atcctgataa agtgaccagg tgtcagttct            50

<210> SEQ ID NO 25
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      R

<400> SEQUENCE: 25
atccaggcca cctaaaatat agaagtctaa agtgaccagg tgtcagttct            50

<210> SEQ ID NO 26
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      S
```

```
<400> SEQUENCE: 26
atccaggcca tctaaaatat agaatgataa agtgaccagg tgtcagttct              50

<210> SEQ ID NO 27
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      Z

<400> SEQUENCE: 27
atccaggcca cctaaaatat agaatgataa agtgactagg tgtcagttct              50

<210> SEQ ID NO 28
<211> LENGTH: 47
<212> TYPE: DNA
<213> ORGANISM: Artificial
<220> FEATURE:
<221> NAME/KEY: misc_feature
<223> OTHER INFORMATION: Description of Artificial Sequence: probe Xbra
      B

<400> SEQUENCE: 28
atccaggcca cctatataga atgataaagt gaccaggtgt cagttct                 47

<210> SEQ ID NO 29
<211> LENGTH: 47
<212> TYPE: DNA
<213> ORGANISM: Artificial
<220> FEATURE:
<221> NAME/KEY: misc_feature
<223> OTHER INFORMATION: Description of Artificial Sequence: probe Xbra
      C

<400> SEQUENCE: 29
atccaggcca cctaaaatat agaatgatgt gaccaggtgt cagttct                 47

<210> SEQ ID NO 30
<211> LENGTH: 40
<212> TYPE: DNA
<213> ORGANISM: Artificial
<220> FEATURE:
<221> NAME/KEY: misc_feature
<223> OTHER INFORMATION: Description of Artificial Sequence: probe Xbra
      U

<400> SEQUENCE: 30
atccaggcca cctaaaatat agtgaccagg tgtcagttct                         40

<210> SEQ ID NO 31
<211> LENGTH: 46
<212> TYPE: DNA
<213> ORGANISM: Artificial
<220> FEATURE:
<221> NAME/KEY: misc_feature
<223> OTHER INFORMATION: Description of Artificial Sequence: probe Xbra
      EE

<400> SEQUENCE: 31
taaagtgacc aggtgtcagt tcttaaagtg accaggtgtc agttct                  46

<210> SEQ ID NO 32
<211> LENGTH: 46
<212> TYPE: DNA
<213> ORGANISM: Artificial
```

```
<220> FEATURE:
<221> NAME/KEY: misc_feature
<223> OTHER INFORMATION: Description of Artificial Sequence: probe Xbra
      ErE

<400> SEQUENCE: 32
agaactgaca cctggtcact ttataaagtg accaggtgtc agttct                      46

<210> SEQ ID NO 33
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      FrF

<400> SEQUENCE: 33
atccaggcca cctaaaatat agaatattct atattttagg tggcctggat                  50

<210> SEQ ID NO 34
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      V

<400> SEQUENCE: 34
atccaggcag gtgtaaatat agaatgataa agtgacccac ctacagttct                  50

<210> SEQ ID NO 35
<211> LENGTH: 50
<212> TYPE: DNA
<213> ORGANISM: Artificial
<220> FEATURE:
<221> NAME/KEY: misc_feature
<223> OTHER INFORMATION: Description of Artificial Sequence: probe Xbra
      W

<400> SEQUENCE: 35
atccaggcag gtgtaaatat agaatgataa agtgaccagg tgtcagttct                  50

<210> SEQ ID NO 36
<211> LENGTH: 60
<212> TYPE: DNA
<213> ORGANISM: Artificial
<220> FEATURE:
<221> NAME/KEY: misc_feature
<223> OTHER INFORMATION: Description of Artificial Sequence: probe alfa
      4I WT (alfa 4 integrin)

<400> SEQUENCE: 36
gcagggcaca cctggattgc attagaatga gactcactac ccagttcagg tgtgttgcgt       60

<210> SEQ ID NO 37
<211> LENGTH: 60
<212> TYPE: DNA
<213> ORGANISM: Artificial
<220> FEATURE:
<221> NAME/KEY: misc_feature
<223> OTHER INFORMATION: Description of Artificial Sequence: probe alfa
      4I A (alfa 4 integrin)

<400> SEQUENCE: 37
gcagggcaca cctggattgc attagaatga gactcactac ccagttcaga tgtgttgcgt       60
```

<210> SEQ ID NO 38
<211> LENGTH: 60
<212> TYPE: DNA
<213> ORGANISM: Artificial
<220> FEATURE:
<221> NAME/KEY: misc_feature
<223> OTHER INFORMATION: Description of Artificial Sequence: probe alfa
      4 I B (alfa 4 integrin)

<400> SEQUENCE: 38
gcagggcaca tctggattgc attagaatga gactcactac ccagttcagg tgtgttgcgt     60

<210> SEQ ID NO 39
<211> LENGTH: 70
<212> TYPE: DNA
<213> ORGANISM: Artificial
<220> FEATURE:
<221> NAME/KEY: misc_feature
<223> OTHER INFORMATION: Description of Artificial Sequence: probe Ecad
      WT

<400> SEQUENCE: 39
tggccggcag gtgaaccctc agccaatcag cggtacgggg ggcggtgctc cggggctcac     60
ctggctgcag                                                            70

<210> SEQ ID NO 40
<211> LENGTH: 70
<212> TYPE: DNA
<213> ORGANISM: Artificial
<220> FEATURE:
<221> NAME/KEY: misc_feature
<223> OTHER INFORMATION: Description of Artificial Sequence: probe Ecad
      A

<400> SEQUENCE: 40
tggccggcag gtgaaccctc agccaatcag cggtacgggg ggcggtgctc cggggctcat     60
ctggctgcag                                                            70

<210> SEQ ID NO 41
<211> LENGTH: 70
<212> TYPE: DNA
<213> ORGANISM: Artificial
<220> FEATURE:
<221> NAME/KEY: misc_feature
<223> OTHER INFORMATION: Description of Artificial Sequence: probe Ecad
      B

<400> SEQUENCE: 41
tggccggcag atgaaccctc agccaatcag cggtacgggg ggcggtgctc cggggctcac     60
ctggctgcag                                                            70

<210> SEQ ID NO 42
<211> LENGTH: 21
<212> TYPE: DNA
<213> ORGANISM: Artificial
<220> FEATURE:
<221> NAME/KEY: misc_feature
<223> OTHER INFORMATION: Description of Artificial Sequence: PCR primer
      for E cadherin promoter sequence ( 341/+41)

<400> SEQUENCE: 42
acaaaagaac tcagccaagt g                                               21

<210> SEQ ID NO 43
<211> LENGTH: 18

<210> SEQ ID NO 43
<211> LENGTH: 18
<212> TYPE: DNA
<213> ORGANISM: Artificial
<220> FEATURE:
<221> NAME/KEY: misc_feature
<223> OTHER INFORMATION: Description of Artificial Sequence: PCR primer
for E cadherin promoter sequence ( 341/+41)

<400> SEQUENCE: 43
ccgcaagctc acaggtgc                                              18

<210> SEQ ID NO 44
<211> LENGTH: 26
<212> TYPE: DNA
<213> ORGANISM: Artificial
<220> FEATURE:
<221> NAME/KEY: misc_feature
<223> OTHER INFORMATION: Description of Artificial Sequence: forward
primer E box1

<400> SEQUENCE: 44
gctgtggccg gcagatgaac cctcag                                     26

<210> SEQ ID NO 45
<211> LENGTH: 26
<212> TYPE: DNA
<213> ORGANISM: Artificial
<220> FEATURE:
<221> NAME/KEY: misc_feature
<223> OTHER INFORMATION: Description of Artificial Sequence: reverse
primer E box1

<400> SEQUENCE: 45
ctgagggttc atctgccggc cacagc                                     26

<210> SEQ ID NO 46
<211> LENGTH: 24
<212> TYPE: DNA
<213> ORGANISM: Artificial
<220> FEATURE:
<221> NAME/KEY: misc_feature
<223> OTHER INFORMATION: Description of Artificial Sequence: forward
primer E box3

<400> SEQUENCE: 46
gctccgggct catctggctg cagc                                       24

<210> SEQ ID NO 47
<211> LENGTH: 25
<212> TYPE: DNA
<213> ORGANISM: Artificial
<220> FEATURE:
<221> NAME/KEY: misc_feature
<223> OTHER INFORMATION: Description of Artificial Sequence: reverse
primer E box3

<400> SEQUENCE: 47
gctgcagcca gatgagcccc ggagc                                      25

<210> SEQ ID NO 48
<211> LENGTH: 27
<212> TYPE: DNA
<213> ORGANISM: Artificial
<220> FEATURE:
<221> NAME/KEY: misc_feature
<223> OTHER INFORMATION: Description of Artificial Sequence: degenerated
primer
<220> FEATURE:
<221> NAME/KEY: misc_feature
<222> LOCATION: (25)

<223> OTHER INFORMATION: n is a spacer and may be any nucleotide

<400> SEQUENCE: 48
cttccagcag ccctacgayc argcnca                               27

<210> SEQ ID NO 49
<211> LENGTH: 28
<212> TYPE: DNA
<213> ORGANISM: Artificial
<220> FEATURE:
<221> NAME/KEY: misc_feature
<223> OTHER INFORMATION: Description of Artificial Sequence: degenerated
      primer
<220> FEATURE:
<221> NAME/KEY: misc_feature
<222> LOCATION: (26)
<223> OTHER INFORMATION: n is a spacer and may be any nucleotide

<400> SEQUENCE: 49
gggtgtggga ccggatrtgc atyttnat                              28

<210> SEQ ID NO 50
<211> LENGTH: 29
<212> TYPE: PRT
<213> ORGANISM: Artificial
<220> FEATURE:
<223> OTHER INFORMATION: SIP1nzf1

<400> SEQUENCE: 50

Gln Leu Leu Thr Cys Pro Tyr Cys Asp Arg Gly Tyr Lys Arg Leu Thr
1               5                   10                  15

Ser Leu Lys Glu His Ile Lys Tyr Arg His Lys Asn Glu
            20                  25

<210> SEQ ID NO 51
<211> LENGTH: 29
<212> TYPE: PRT
<213> ORGANISM: Artificial
<220> FEATURE:
<223> OTHER INFORMATION: sigma-EF1nzf1

<400> SEQUENCE: 51

Gln Leu Leu Thr Cys Pro Tyr Cys Asp Arg Gly Tyr Lys Arg Phe Thr
1               5                   10                  15

Ser Leu Lys Glu His Ile Lys Tyr Arg His Lys Asn Glu
            20                  25

<210> SEQ ID NO 52
<211> LENGTH: 28
<212> TYPE: PRT
<213> ORGANISM: Artificial
<220> FEATURE:
<223> OTHER INFORMATION: SIP1nzf2

<400> SEQUENCE: 52

Glu Asn Phe Ser Cys Pro Leu Cys Ser Tyr Thr Phe Ala Tyr Arg Thr
1               5                   10                  15

Gln Leu Glu Arg His Met Val Thr His Lys Pro Gly
            20                  25

<210> SEQ ID NO 53
<211> LENGTH: 28
<212> TYPE: PRT
<213> ORGANISM: Artificial
<220> FEATURE:
<223> OTHER INFORMATION: sigma-EF1nzf2

<400> SEQUENCE: 53

Glu Asn Phe Ser Cys Ser Leu Cys Ser Tyr Thr Phe Ala Tyr Arg Thr
1               5                   10                  15

Gln Leu Glu Arg His Met Thr Ser His Lys Ser Gly
            20                  25

<210> SEQ ID NO 54
<211> LENGTH: 28
<212> TYPE: PRT
<213> ORGANISM: Artificial
<220> FEATURE:
<223> OTHER INFORMATION: SIP1nzf3 and sigma-EF1nzf3

<400> SEQUENCE: 54

Arg Lys Phe Lys Cys Thr Glu Cys Gly Lys Ala Phe Lys Tyr Lys His
1               5                   10                  15

His Leu Lys Glu His Leu Arg Ile His Ser Gly Glu
            20                  25

<210> SEQ ID NO 55
<211> LENGTH: 28
<212> TYPE: PRT
<213> ORGANISM: Artificial
<220> FEATURE:
<223> OTHER INFORMATION: SIP1nzf4 and sigma-EF1nzf4

<400> SEQUENCE: 55

Lys Pro Tyr Glu Cys Pro Asn Cys Lys Lys Arg Phe Ser His Ser Gly
1               5                   10                  15

Ser Tyr Ser Ser His Ile Ser Ser Lys Lys Cys Ile
            20                  25

<210> SEQ ID NO 56
<211> LENGTH: 28
<212> TYPE: PRT
<213> ORGANISM: Artificial
<220> FEATURE:
<223> OTHER INFORMATION: SIP1czf1

<400> SEQUENCE: 56

Gly Met Tyr Ala Cys Asp Leu Cys Asp Lys Thr Phe Gln Lys Ser Ser
1               5                   10                  15

Ser Leu Leu Arg His Lys Tyr Glu His Thr Gly Lys
            20                  25

<210> SEQ ID NO 57
<211> LENGTH: 28
<212> TYPE: PRT
<213> ORGANISM: Artificial
<220> FEATURE:
<223> OTHER INFORMATION: sigma-EF1czf1

<400> SEQUENCE: 57

Gly Met Tyr Ala Cys Asp Leu Cys Asp Lys Ile Phe Gln Lys Ser Ser
1               5                   10                  15

Ser Leu Leu Arg His Lys Tyr Glu His Thr Gly Lys
            20                  25

<210> SEQ ID NO 58
<211> LENGTH: 28
<212> TYPE: PRT
<213> ORGANISM: Artificial
<220> FEATURE:

<223> OTHER INFORMATION: SIP1czf2

<400> SEQUENCE: 58

Arg Pro His Gln Cys Gln Ile Cys Lys Lys Ala Phe Lys His Lys His
1               5                   10                  15

His Leu Ile Glu His Ser Arg Leu His Ser Gly Glu
            20                  25

<210> SEQ ID NO 59
<211> LENGTH: 28
<212> TYPE: PRT
<213> ORGANISM: Artificial
<220> FEATURE:
<223> OTHER INFORMATION: sigma-EF1czf2

<400> SEQUENCE: 59

Arg Pro His Gln Cys Gly Ile Cys Arg Lys Ala Phe Lys His Lys His
1               5                   10                  15

His Leu Ile Glu His Met Arg Leu His Ser Gly Glu
            20                  25

<210> SEQ ID NO 60
<211> LENGTH: 28
<212> TYPE: PRT
<213> ORGANISM: Artificial
<220> FEATURE:
<223> OTHER INFORMATION: SIP1czf3 and sigma-EF1czf3

<400> SEQUENCE: 60

Glu Lys Pro Tyr Cys Asp Lys Cys Gly Lys Arg Phe Ser His Ser Gly
1               5                   10                  15

Ser Tyr Ser Gln His Met Asn His Arg Tyr Ser Tyr
            20                  25

<210> SEQ ID NO 61
<211> LENGTH: 52
<212> TYPE: PRT
<213> ORGANISM: Artificial
<220> FEATURE:
<223> OTHER INFORMATION: SIP1nzf3+nzf4

<400> SEQUENCE: 61

Cys Thr Glu Cys Gly Lys Ala Phe Lys Tyr Lys His His Leu Lys Glu
1               5                   10                  15

His Leu Arg Ile His Ser Gly Glu Lys Pro Tyr Glu Cys Pro Asn Cys
            20                  25                  30

Lys Lys Arg Phe Ser His Ser Gly Ser Tyr Ser Ser His Ile Ser Ser
        35                  40                  45

Lys Lys Cys Ile
    50

<210> SEQ ID NO 62
<211> LENGTH: 54
<212> TYPE: PRT
<213> ORGANISM: Artificial
<220> FEATURE:
<223> OTHER INFORMATION: SIP1czf2+czf3

<400> SEQUENCE: 62

Cys Gln Ile Cys Lys Lys Ala Phe Lys His Lys His His Leu Ile Glu
1               5                   10                  15

His Ser Arg Leu His Ser Gly Glu Lys Pro Tyr Gln Cys Asp Lys Cys
            20                  25                  30

```
Gly Lys Arg Phe Ser His Ser Gly Ser Tyr Ser Gln His Met Asn His
         35                  40                  45

Arg Tyr Ser Tyr Cys Lys
    50

<210> SEQ ID NO 63
<211> LENGTH: 52
<212> TYPE: PRT
<213> ORGANISM: Artificial
<220> FEATURE:
<223> OTHER INFORMATION: sigma-EF1nzf3+nzf4

<400> SEQUENCE: 63

Cys Thr Glu Cys Gly Lys Ala Phe Lys Tyr Lys His His Leu Lys Glu
1               5                   10                  15

His Leu Arg Ile His Ser Gly Glu Lys Pro Tyr Glu Cys Pro Asn Cys
            20                  25                  30

Lys Lys Arg Phe Ser His Ser Gly Ser Tyr Ser Ser His Ile Ser Ser
         35                  40                  45

Lys Lys Cys Ile
    50

<210> SEQ ID NO 64
<211> LENGTH: 54
<212> TYPE: PRT
<213> ORGANISM: Artificial
<220> FEATURE:
<223> OTHER INFORMATION: sigma-EF1czf2+czf3

<400> SEQUENCE: 64

Cys Gly Ile Cys Lys Lys Ala Phe Lys His Lys His His Leu Ile Glu
1               5                   10                  15

His Met Arg Leu His Ser Gly Glu Lys Pro Tyr Gln Cys Asp Lys Cys
            20                  25                  30

Gly Lys Arg Phe Ser His Ser Gly Ser Tyr Ser Gln His Met Asn His
         35                  40                  45

Arg Tyr Ser Tyr Cys Lys
    50

<210> SEQ ID NO 65
<211> LENGTH: 14
<212> TYPE: DNA
<213> ORGANISM: Artificial
<220> FEATURE:
<221> NAME/KEY: misc_feature
<223> OTHER INFORMATION: Description of Artificial Sequence: a class of
      zinc finger
<220> FEATURE:
<221> NAME/KEY: misc_feature
<222> LOCATION: (2)...(3), (5)...(8), (10)...(13)
<223> OTHER INFORMATION: n is a spacer and may be any nucleotide

<400> SEQUENCE: 65
cnncnnnnhn nnnc                                                        14

<210> SEQ ID NO 66
<211> LENGTH: 25
<212> TYPE: DNA
<213> ORGANISM: Artificial
<220> FEATURE:
<221> NAME/KEY: misc_feature
<223> OTHER INFORMATION: Description of Artificial Sequence: a class of
      zinc finger
<220> FEATURE:
```

-continued

```
<221> NAME/KEY: misc_feature
<222> LOCATION: (2)...(6), (8)...(19), (21)...(24)
<223> OTHER INFORMATION: n is a spacer and may be any nucleotide

<400> SEQUENCE: 66
cnnnnncnnn nnnnnnnnnh nnnnc                                              25
```